US009856313B2

(12) United States Patent
Zheng et al.

(10) Patent No.: US 9,856,313 B2
(45) Date of Patent: Jan. 2, 2018

(54) EPITOPE OF RSV FUSION PROTEIN AND ANTIBODY RECOGNIZING THE SAME

(71) Applicants: XIAMEN UNIVERSITY, Xiamen (CN); THE UNITED STATES OF AMERICA, AS REPRESENTED BY THE SECRETARY, DEPARTMENT OF HEALTH AND HUMAN SERVICES, Washington, DC (US); XIAMEN INNOVAX BIOTECH CO., LTD., Xiamen (CN)

(72) Inventors: Zizheng Zheng, Xiamen (CN); Jason S. McLellan, Hanover, NH (US); Man Chen, Bethesda, MD (US); Min Zhao, Xiamen (CN); Liangmin Huang, Xiamen (CN); Barney S. Graham, Bethesda, MD (US); Ningshao Xia, Xiamen (CN)

(73) Assignees: XIAMEN UNIVERSITY, Xiamen (CN); XIAMEN INNOVAX BIOTECH CO., LTD., Xiamen (CN); THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 100 days.

(21) Appl. No.: 14/777,275

(22) PCT Filed: Mar. 17, 2014

(86) PCT No.: PCT/CN2014/073505
§ 371 (c)(1),
(2) Date: Sep. 15, 2015

(87) PCT Pub. No.: WO2014/139476
PCT Pub. Date: Sep. 18, 2014

(65) Prior Publication Data

US 2016/0031972 A1 Feb. 4, 2016

(30) Foreign Application Priority Data

Mar. 15, 2013 (CN) .......................... 2013 1 0082338

(51) Int. Cl.

| | |
|---|---|
| ***C07K 16/10*** | (2006.01) |
| ***A61K 31/7084*** | (2006.01) |
| ***C07K 14/005*** | (2006.01) |
| ***A61K 39/155*** | (2006.01) |
| ***C12N 7/00*** | (2006.01) |
| *A61K 39/12* | (2006.01) |
| *A61K 39/00* | (2006.01) |

(52) U.S. Cl.
CPC ...... *C07K 16/1027* (2013.01); *A61K 31/7084* (2013.01); *A61K 39/155* (2013.01); *C07K 14/005* (2013.01); *C12N 7/00* (2013.01); *A61K 39/12* (2013.01); *A61K 2039/53* (2013.01); *C07K 2317/20* (2013.01); *C07K 2317/21* (2013.01); *C07K 2317/24* (2013.01); *C07K 2317/31* (2013.01); *C07K 2317/34* (2013.01); *C07K 2317/51* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/76* (2013.01); *C07K 2319/00* (2013.01); *C07K 2319/35* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 5,866,125 | A | 2/1999 | Brams et al. |
| 2010/0239593 | A1 | 9/2010 | Spits et al. |
| 2012/0070446 | A1 | 3/2012 | Beaumont et al. |

FOREIGN PATENT DOCUMENTS

| | | | |
|---|---|---|---|
| CN | 101778866 | A | 7/2010 |
| CN | 102210860 | A | 10/2011 |
| CN | 102712692 | A | 10/2012 |
| EP | 2486053 | A1 | 8/2012 |
| WO | 2008147196 | A2 | 12/2008 |
| WO | 2011043643 | A1 | 4/2011 |

(Continued)

OTHER PUBLICATIONS

Jun. 16, 2014—(WO) International Search Report—App PCT/CN2014/073505.

(Continued)

*Primary Examiner* — Shanon A. Foley
*Assistant Examiner* — Myron G Hill
(74) *Attorney, Agent, or Firm* — Banner & Witcoff, Ltd.

(57) ABSTRACT

The present invention relates to an epitope peptide (or a variant thereof) which can be used in the prevention of respiratory syncytial virus (RSV) infection, a recombinant protein comprising the epitope peptide (or a variant thereof) and a carrier protein, and uses of the epitope peptide (or a variant thereof) and the recombinant protein. The present invention also relates to an antibody against the epitope peptide, a cell line for generating the antibody, and uses thereof. Furthermore, the present invention also relates to a vaccine or a pharmaceutical composition comprising the recombinant protein or the antibody according to the invention, for preventing one or more symptoms associated with RSV infection.

17 Claims, 8 Drawing Sheets

(56) References Cited

FOREIGN PATENT DOCUMENTS

WO 2012006596 A2 1/2012

OTHER PUBLICATIONS

Arbiza et al., "Characterization of two antigenic sites recognized by neutralizing monoclonal antibodies directed against the fusion glycoprotein of human respiratory syncytial virus," Journal of General Virology, vol. 73, No. 9, pp. 2225-2234, Jan. 1, 1992.

Extended European Search Report for Application No. 14765573.2, dated Mar. 3, 2017.

McLellan et al., "Structure of RSV Fusion Glycoprotein Trimer Bound to a Prefusion-Specific Neutralizing Antibody", Science, vol. 340, No. 6136, pp. 1113-1117, Apr. 25, 2013.

Schepens et al., "Nanobodies(R) Specific for Respiratory Syncytial Virus Fusion Protein Protect Against Infection by Inhibition of Fusion", Journal of Infectious Diseases, vol. 204, No. 11, pp. 1692-1701, Oct. 12, 2011.

Swanson et al., "Structural basis for immunization with postfusion respiratory syncytial virus fusion F glycoprotein (RSV F) to elicit high neutralizing antibody titers," PNAS, vol. 108, No. 23, pp. 9619-9624, Jun. 7, 2011.

EPITOPE OF RSV FUSION PROTEIN AND ANTIBODY RECOGNIZING THE SAME

TECHNICAL FIELD

The invention relates to the field of molecular virology, particularly the field concerning vaccines against Respiratory syncytial virus (RSV). In particular, the invention relates to an epitope peptide (or a variant thereof) for the prevention of RSV infection, and a recombinant protein comprising the epitope peptide (or a variant thereof) and a carrier protein, and uses of the epitope peptide (or a variant thereof) and the recombinant protein. The invention also relates to an antibody against the epitope peptide, a nucleic acid molecule encoding the antibody, a cell line for generating the antibody, and uses thereof. The invention further relates to a vaccine or a pharmaceutical composition comprising the recombinant protein or the antibody according to the invention, for preventing one or more symptoms associated with RSV infection.

BACKGROUND ART

Human Respiratory syncytial virus (RSV) has been the most important pathogen responsible for lower respiratory infection in infants since it was discovered in 1950s. In USA, RSV is the main reason why infants under the age of 1 are hospitalized (D. K. Shay, R. C. Holman. et al., JAMA, 282 (1999) 1440-1446), and one of the main reasons why children under the age of 5 are in clinical diagnosis (C. B. Hall, G. A. Weinberg, et al., N Engl J Med, 360 (2009) 588-598). There are more than 30 million cases of lower respiratory infection caused by RSV in the whole world, and more than 3 million of them have to be hospitalized. RSV is the most common reason why children under the age of 5 are hospitalized (H. Nair, W. A. Brooks, et al., Lancet, 378 (2011) 1917-1930). The RSV infection rate reaches up to 50-70% for premature babies, infants with bronchial and pulmonary hypoplasia, infants with congenital heart disease and infants with immunodeficiency (A. C. Cooper, N. C. Banasiak, P. J. Allen, Pediatr Nurs, 29 (2003) 452-456). The death of 160-600 thousands of children is associated with RSV every year (T. S. Howard, L. H. Hoffman, et al. J Pediatr, 137 (2000) 227-232; S. Leader, K. Kohlhase. J Pediatr, 143 (2003) S127-132). Period for hospitalization of infants infected with RSV can be of 2.5 months, and the hospitalization costs thus incurred may reach up to 0.36-0.57 billion dollars each year in USA (E. A. Simoes. Lancet, 354 (1999) 847-852). Old people are also susceptible to RSV, and there are more than 12000 old people died of RSV infection each year, accounting for about ⅓ of influenza mortality in the same group of people (A. R. Falsey, P. A. Hennessey, et al. N Engl J Med, 352 (2005) 1749-1759; W. W. Thompson, D. K. Shay, E. Weintraub, et al., JAMA, 289 (2003) 179-186). In China, due to the lack of RSV diagnostic agents developed in China, RSV detection is high in cost and therefore is not widely applied; thus, the epidemic situation and harmfulness of RSV are not quite clear in China so far; however, the studies on some areas show that RSV infection is also an important factor responsible for inducing lower respiratory infection in Chinese children (Xu Guanren, Sun Songwen, Xu Xuqing et al., Chinese Journal of Disease Control & Prevention, 4 (2000) 37-39; Xie Jianping, He Cuijuan, et al., Chinese Journal of Pediatrics, 35 (1997) 402-403; Zhu Runan, Deng Jie, Wang Fang et al., 21 (2003) 25-28).

Up to now, there are still no safe and effective vaccines against RSV. Only one neutralization antibody (Palivizumab, Trade name: Synagis) recognizing RSV epitope, a fusion glycoprotein F, can generate a passive immunization effect in newborns and therefore reduce the incidence in newborns. The antibody agent is approved to be applicable to premature babies, and high risk infants having chronic lung diseases, bronchial and pulmonary dysplasia, or congenital heart disease (H. W. Kim, J. G. Canchola, C. D. Brandt, et al. Am J Epidemiol, 89 (1969) 422-434), to prevent serious lower respiratory infection caused by RSV. The antibody agent has a low neutralizing titer and is high in production cost, and thus is very expensive on the market, and its application is limited to infants having a high risk of infection and cannot be applied widely.

The application of Syangis shows that neutralizing monoclonal antibodies binding to RSV-F protein may be used in clinical protection, and F protein contains effective, neutralization-active sites. Moreover, F protein is on the surface of a virus, and is necessary for entry into cell and formation of syncytia. Hence, F protein is an important target protein for screening preventive and protective antibodies. RSV, a negative-sense, single-stranded, non-segmented RNA virus of the genus *pneumovirus*, the family Paramyxoviridae, has 15222 nucleotides and encodes 10 main proteins. F protein, which has a full length of 574 amino acids, is an N-glycosylated type I transmembrane glycoprotein, and is an important surface molecule as the main transmembrane protein during RSV infection. It is still not clear yet with respect to membrane-fusion mechanism and triggering process of F protein. It is speculated that since pre-fusion F conformation (pre-fusion F, pre-F) is in a metastable and high energy state, a change in conformation occurs upon binding to a target cell, to form a highly stable post-fusion F protein (post-fusion F, post-F), resulting in the fusion of a viral membrane to a cell membrane. Since the free energy difference between metastable pre-F conformation and stable post-F conformation is significant, the membrane fusion process is not reversible. McLellan et al. (J. S. McLellan, M. Chen, J. S. Chang, et al. J Virol, 84 (2010) 12236-12244) obtained a stable post-F protein structure by utilizing a mammalian expression system.

Since pre-F protein is not structurally stable and has several intermediates, it is very difficult to study the structure of pre-F protein by means of preparing crystals. Therefore, McLellan et al. (J. S. McLellan, M. Chen, J. S. Chang, et al. J Virol, 84 (2010) 12236-12244) stimulated and predicted the structure of RSV pre-F protein by virtue of HPIV3 pre-F protein with a known structure, and proposed that RSV F protein might have a pre-F conformation and also proposed the above hypothesis for the fusion mechanism. It still needs to be further confirmed by the obtainment of a stable pre-F conformation protein with respect to the accurate structure of pre-F conformation, and the conformation changing process during fusion.

Now, most of antibodies for studying antigen epitopes of F protein were isolated from BalB/c mice, and neutralizing epitopes were identified by methods such as peptide mapping, antibody competition, and escape mutations. F protein, as one of the most important surface structural proteins of viruses, has a lot of neutralization antibody-recognizing epitopes on the surface. Currently known neutralization antibodies of RSV F protein are mainly directed to the following antigen epitopes (J. S. McLellan, Y. Yang, et al. J Virol, 85 (2011) 7788-7796; M. Magro, D. Andreu, et al. J Virol, 84 (2010) 7970-7982.).

Epitope I: antibodies against epitope I include commercially available prophylactic monoclonal antibody Synagis and its equivalent derivative motavizumab, which recognize an epitope on F1 that includes residues a.a.255-a.a.275. McLellan et al. (J. S. McLellan, M. Chen, J. S. Chang, et al., J Virol, 84 (2010) 12236-12244.) demonstrated by analyzing the crystal structures of motavizumab monoclonal antibody and the peptide of a.a.253-a.a.277 residues of F protein, that the region forms a "helix-loop-helix" based on secondary structure. The crystal structure revealed that motavizumab monoclonal antibody bound to one face of the "helix-loop-helix", and made hydrogen bond or salt bridge interactions with Asn268 and Lys272, the mutation of which may result in antibody escape. Antigen epitope A, which motavizumab binds to, is remarkably well-preserved in the post-fusion structure, and the antibody binding sites are sufficiently exposed. The structures of motavizumab and post-F protein reveal the mechanism that Synagis and motavizumab monoclonal antibodies have neutralizing activity. The modeling of RSV pre-F protein structure suggests that this epitope is present inside the conformation of pre-F protein, and cannot be exposed in naturally occurring RSV F protein. Graham et al. demonstrated that Synagis and motavizumab monoclonal antibodies can only inhibit the fusion of RSV to a cell, but cannot inhibit the absorption of RSV (J. S. McLellan, Y. Yang, et al. J Virol, 85 (2011) 7788-7796; J. S. McLellan, M. Chen, A. Kim, et al. Nat Struct Mol Biol, 17 (2010) 248-250). Certainly, it can only be confirmed by the crystal structure of pre-F protein.

Epitope II: the antibodies recognizing epitope II include 131-2a, which recognizes the cysteine-rich domain of F1. The antibody can block RSV viral infection by up to 50%, indicating that the epitope has post-translation heterogeneity, or the antibodies exert a neutralization action by indirect effect such as coagulation of viruses. Unlike antibodies recognizing epitope A and epitope C, the antibodies partially block the absorption of viruses to a target cell. It is possible that the epitope is close to the cell membrane of the virus in the conformation of pre-F protein, but is on the top in the conformation of post-F protein.

Epitope IV: the recognition region is a.a.422-a.a.438, which is the target for monoclonal antibodies such as 19 and 101F. The epitope is in the relatively conservative region of F1 conformation. McLellan et al. (J. S. McLellan, Y. Yang, et al. J Virol, 85 (2011) 7788-7796) have obtained the crystal structure of the complex of 101F and the peptide fragment (a.a.422-a.a.438) of F protein. The core epitope in this region is a.a.427-a.a.437, and it is known that escape mutations Arg429 and Lys433 interacts with 101F by hydrogen bond and salt bridge interactions. The affinity of 101F to a free peptide is thousands of times lower than its affinity to post-F. 101F shows in the post-F structure that the epitope of 101 F is more complex than a linear peptide.

Neutralization antibodies against said three epitopes are little improved as compared to the commercially available Synagis in terms of neutralizing titer, and are reactive with both pre-F and post-F. Therefore, it will lay fundations for prevention and treatment of RSV that monoclonal antibodies against pre-F having higher neutralizing activity are screened by using RSV F protein as target.

Contents of Invention

In the invention, unless otherwise specified, the scientific and technical terms used herein have the meanings as generally understood by a person skilled in the art. Moreover, the laboratory operations of cell culture, molecular genetics, nucleic acid chemistry and immunology used herein are the routine operations widely used in the corresponding fields. Meanwhile, in order to better understand the invention, the definitions and explanations of the relevant terms are provided as follows.

As used herein, the term "RSV fusion protein" or "F protein" refers to fusion protein (F protein) of respiratory syncytial virus (RSV), which is well known by a person skilled in the art (see, e.g. NCBI GENBANK Accession No: P03420).

As used herein, when the amino acid sequence of F protein is mentioned, it is described by the sequence set forth in SEQ ID NO: 15. For example, the expression "amino acid residues from positions 196 to 209 of F protein" refers to the amino acid residues from positions 196 to 209 of the polypeptide set forth in SEQ ID NO: 15. However, a person skilled in the art understands that mutations or variations (including, but not limited to, substitution, deletion and/or addition, for example, F protein of a different genotype or a different gene subtype) may occur naturally in or be introduced artificially into the amino acid sequence of F protein without affecting its biological properties. Therefore, in the invention, the term "F protein" intends to include all such polypeptides, for example, including the sequence set forth in SEQ ID NO: 15 and its natural or artificial variants. In addition, when sequence fragments of F protein are described, they include not only the sequence fragments of SEQ ID NO: 15, but also the corresponding sequence fragments of its natural or artificial variants. For example, the expression "amino acid residues from positions 196 to 209 of F protein" comprises amino acid residues from positions 196 to 209 of SEQ ID NO: 15 and the corresponding fragments of its variants (natural or artificial variants). According to the invention, the expression "corresponding sequence fragments" or "corresponding fragments" refers to fragments that are located in equal positions of sequences when the sequences are subjected to optimized alignment, namely, the sequences are aligned to obtain a highest percentage of identity.

Previous research show that F protein has one identified conformation, post-F. McLellan et al. deduced from the research results on F protein of parainfluenza virus (PIV) that F protein of RSV may have a pre-F conformation (McLellan et al., (2010), J Vriol, 84:12236-12244). In general, pre-F conformation is metastable, which will spontaneously convert to stable post-F conformation. Therefore, the expressed and purified F protein from cells is mainly present in post-F conformation (McLellan et al., (2010), J Vriol, 84: 12236-12244).

As used herein, the term "pre-F protein" refers to F protein present in pre-F conformation. As used herein, the term "post-F protein" refers to F protein present in post-F conformation.

As used herein, the term "antibody" generally refers to an immunoglobulin molecule consisting of two pairs of polypeptide chains (each has a light (L) chain and a heavy (H) chain). Light chains of an antibody may be classified into K and A light chain. Heavy chains may be classified into μ, δ, γ, α and ϵ, which define isotypes of an antibody as IgM, IgD, IgG, IgA and IgE, respectively. In a light chain and a heavy chain, a variable region is linked to a constant region via a "J" region of about 12 or more amino acids, and a heavy chain further comprises a "D" region of about 3 or more amino acids. Each heavy chain consists of a heavy chain variable region ($V_H$) and a heavy chain constant region ($C_H$). A heavy chain constant region consists of 3 domains ($C_H1$, $C_H2$ and $C_H3$). Each light chain consists of a light chain variable region ($V_L$) and a light chain constant region ($C_L$). A light chain constant region consists of a domain $C_L$. The constant region of an antibody can mediate the binding of an immunoglobulin to a host tissue or factor, including various cells (e.g., effector cells) of an immune system and a first component (C1q) of classical complement system. $V_H$ and $V_L$ region can further be divided into hypervariable regions (called complementary determining regions (CDR)), which are interspaced by relatively conservative regions (called framework region (FR)). Each $V_H$ and $V_L$ consists of 3 CDRs and 4 FRs in the following order: FR1, CDR1, FR2, CDR2, FR3, CDR3, FR4 from N-terminal to C-terminal. The variable region ($V_H$ and $V_L$) of each heavy/light chain pair forms antigen binding sites, respectively. Distribution of amino acids in various regions or domains follows the definition in Kabat Sequences of Proteins of Immunological Interest (National Institutes of Health, Bethesda, Md. (1987 and 1991)), or Chothia & Lesk (1987) J. Mol. Biol. 196: 901-917; Chothia et al., (1989) Nature 342:878-883. The term "antibody" is not restricted by any specific method for producing antibodies. For example, antibodies include particularly, recombinant antibodies, monoclonal antibodies and polyclonal antibodies. Antibodies may be of different antibody isotypes, for example, IgG (e.g., IgG1, IgG2, IgG3 or IgG4 subtype), IgA1, IgA2, IgD, IgE or IgM antibody.

As used herein, the term "antigen binding fragment" of an antibody refers to polypeptides comprising fragments of a full-length antibody, which retain the ability of specifically binding to an antigen that the full-length antibody specifically binds to, and/or compete with the full-length antibody for binding to the same antigen, also known as "antigen binding portion". Generally, see Fundamental Immunology, Ch. 7 (Paul, W., ed., the second edition, Raven Press, N.Y. (1989), which is incorporated herein by reference for all purposes. Antigen binding fragments of an antibody may be produced by recombinant DNA techniques or by enzymatic or chemical cleavage of an intact antibody. Under some conditions, antigen binding fragments include Fab, Fab', $F(ab')_2$, Fd, Fv, dAb and complementary determining region (CDR) fragments, single chain antibody (e.g. scFv), chimeric antibody, diabody and such polypeptides that comprise at least part of antibody sufficient to confer the specific antigen binding ability on the polypeptides.

As used herein, the term "Fd fragment" refers to antibody fragment consisting of $V_H$ and $C_H1$ domain; the term "Fv fragment" refers to antibody fragment consisting of $V_L$ and $V_H$ domain of a single arm; the term "dAb fragment" refers to antibody fragment consisting of $V_H$ domain (Ward et al., Nature 341:544-546 (1989)); the term "Fab fragment" refers to antibody fragment consisting of $V_L$, $V_H$, $C_L$ and $C_H1$ domain; the term "$F(ab')_2$ fragment" refers to antibody fragment comprising two Fab fragments linked to each other via disulphide bridge(s) on hinge region.

Under some conditions, antigen binding fragments of an antibody are single chain antibodies (e.g. scFv), wherein $V_L$ and $V_H$ domain are paired to form a monovalent molecule via a linker that enables them to produce a single polypeptide chain (see, for example, Bird et al., Science 242:423-426 (1988) and Huston et al., Proc. Natl. Acad. Sci. USA 85:5879-5883 (1988)). Such scFv molecules generally have a common structure: $NH_2$—$V_L$-linker-$V_H$—COOH or $NH_2$—$V_H$-linker-$V_L$—COOH. Suitable linkers in the prior art consist of repeated GGGGS amino acid sequence or variants thereof. For example, a linker having an amino acid sequence $(GGGGS)_4$ may be used, and its variants may also be used (Holliger et al., (1993), Proc. Natl. Acad. Sci. USA 90: 6444-6448). Other linkers that may be used in the invention are described by Alfthan et al., (1995), Protein Eng. 8:725-731, Choi et al., (2001), Eur. J. Immunol. 31: 94-106, Hu et al., (1996), Cancer Res. 56:3055-3061, Kipriyanov et al., (1999), J. Mol. Biol. 293:41-56 and Roovers et al., (2001), Cancer Immunol.

Under some conditions, antigen binding fragments of an antibody may be diabodies, i.e. divalent antibodies, wherein $V_H$ and $V_L$ domain are expressed on a single polypeptide chain; however, the linker used is too short to allow the pairing of the two domains on the same chain; the domains have to be paired with the complementary domains on another chain to produce two antigen binding sites (see, for example, Holliger P. et al., Proc. Natl. Acad. Sci. USA 90:6444-6448 (1993), and Poljak R. J. et al., Structure 2:1121-1123 (1994)).

Antigen binding fragments (e.g. the antibody fragments as described above) of an antibody may be obtained from a given antibody (e.g., the monoclonal antibody 5C4 provided in the invention) by conventional techniques known by a person skilled in the art (e.g., recombinant DNA technique or enzymatic or chemical cleavage methods), and may be screened for specificity in the same manner by which intact antibodies are screened.

In the invention, unless specified definitely, when the term "antibody" is mentioned, it includes not only intact antibodies, but also antigen binding fragments of the antibodies.

As used herein, the term "MAb" and "monoclonal antibody" refer to an antibody or a fragment of an antibody from a population of highly homologous antibody molecules, i.e. a population of completely identical antibody molecules except for natural mutation that may occur spontaneously. A monoclonal antibody has a high specificity for a single epitope of an antigen. Polyclonal antibody, relative to monoclonal antibody, generally comprises at least two or more different antibodies which generally recognize different epitopes on an antigen. Monoclonal antibodies are generally obtained by hybridoma technique reported by Kohler et al. for the first time (Nature, 256:495, 1975), and can also be obtained by recombinant DNA technique (see, for example, U.S. Pat. No. 4,816,567).

For example, monoclonal antibodies may be prepared as follows. Firstly, mice or other suitable host animals are immunized by injection of immunogen (if necessary, adjuvants are added). The injection means of immunogens or adjuvants generally are subcutaneous multi-point injection or intraperitoneal injection. Pre-conjugation of immunogens to some known proteins (e.g. serum albumin or soybean trypsin inhibitor) may promote immunogenicity of antigens in a host. Adjuvants may be Freund's adjuvant or MPL-TDM, etc. After immunization of animal, lymphocytes secreting antibodies that specifically bind to immunogen are produced in the animal. In addition, lymphocytes may be obtained by means of in vitro immunization. Lymphocytes of interest are collected and are fused to myeloma cells using a suitable fusion agent (such as PEG), thereby getting hybridoma cells (Goding, Monoclonal Antibodies: Principles and Practice, pp. 59-103, Academic Press, 1996). The hybridoma cells prepared above are seeded to a sutiable culture medium and grow in the medium, and the culture medium comprises one or more substances capable of inhibiting growth of unfused, parent myeloma cells. For example, in the case of parent myeloma cells deficient in hypoxanthine guanine phosphoribosyl transferase (HGPRT or HPRT), growth of HGPRT-deficient cells is inhibited by the addition of substances such as hypoxanthine, aminopterin and thymine (HAT culture medium) to the culture medium. Preferred myeloma cells should have a high fusion rate, stable ability of secreting antibodies, be sensitive to HAT culture medium, and the like. The first choice of myeloma cells is murine myeloma, such as MOP-21 and MC-11 mouse tumor derived cell line (THE Salk Institute Cell Distribution Center, San Diego, Calif. USA), and SP-2/0 or X63-Ag8-653 cell line (American Type Culture Collection, Rockville, Md. USA). In addition, human myeloma and human-mouse heterogenous myeloma cell lines may be used to prepare human monoclonal antibodies (Kozbor, J. Immunol., 133: 3001 (1984); Brodeur et al., Monoclonal Antibody Production Techniques and Applications, pp. 51-63, Marcel Dekker, Inc., New York, 1987). Culture media for growing hybridoma cells are used to detect the generation of monoclonal antibodies against specific antigens. The following methods may be used to determine the binding specificity of monoclonal antibodies produced in hybridoma cells, immunoprecipitation or in vitro binding assays, such as Radioimmunoassay (RIA) and enzyme linked immunosorbent assay (ELISA). For example, Scatchard assay described in Munson et al., Anal. Biochem. 107: 220 (1980) may be used to determine the affinity of monoclonal antibodies. After determining the specifity, affinity and reactivity of antibodies produced in hybridomas, cell lines of interest may be subcloned by limiting dilution method described in Goding, Monoclonal Antibodies: Principles and Practice, pp. 59-103, Academic Press, 1996. A suitable culture medium may be DMEM or RPMI-1640, etc. In addition, hybridoma cells may grow in a form of ascites tumor in animal bodies. By using traditional methods for purifying immunoglobulins, such as Protein A agarose gel, hydroxyapatite chromatography, gel electrophoresis, dialysis and affinity chromatography, monoclonal antibodies secreted by subclone cells may be isolated from cell culture, ascites or serum.

Monoclonal antibodies may be obtained by genetic engineering recombinant techniques. The nucleic acid primers that specifically bind to MAb heavy chain and light chain gene are subjected to PCR amplification, thereby isolating the DNA molecules encoding MAb heavy chain and light chain from hybridoma cells. The DNA molecules obtained are inserted into an expression vector, host cells (e.g. *E. coli* cells, COS cells, CHO cells, or other myeloma cells that do not produce immunoglobulin) are transfected with them and are cultured under suitable conditions to obtain antibodies of interest by recombinant expression.

As used herein, the term "chimeric antibody" refers to such an antibody wherein a part of its light chain and/or heavy chain is derived from an antibody (which may be originated from a specific species or belongs to a specific antibody type or subtype), and the other part of its light chain and/or heavy chain is derived from another antibody (which may be originated from an identical or different species or belongs to an identical or different antibody type or subtype), provided that the antibody still retains the activity of binding to the antigen of interest (U.S. Pat. No. 4,816,567 to Cabilly et al.; Morrison et al., Proc. Natl. Acad. Sci. USA, 81: 6851-6855 (1984)).

As used herein, the term "humanized antibody" refers to an antibody or antibody fragment in which all the CDR regions or a part of CDR regions of human immunoglobulin (receptor antibody) are replaced with the CDR regions of a non-human antibody (donor antibody), wherein the donor antibody may be non-human (e.g., mouse, rat or rabbit) antibody having the expected specificity, affinity or reactivity. In addition, some amino acids of framework regions (FRs) of a receptor antibody may also be replaced by the corresponding amino acid residues of a non-human antibody, or amino acid residues of another antibody, so as to further improve or optimize the properities of the antibody. With respect to more detailed contents relating to humanized antibodies, see, for example, Jones et al., Nature, 321:522-525 (1986); Reichmann et al., Nature, 332:323-329 (1988); Presta, Curr. Op. Struct. Biol., 2:593-596 (1992); and Clark, Immunol. Today 21: 397-402 (2000).

As used herein, the term "neutralization antibody" refers to an antibody or antibody fragment that can eliminate or significantly reduce virulence (e.g. ability of infecting cells) of viruses of interest.

As used herein, the term "epitope" refers to a portion on antigen that an immunoglobulin or antibody specifically binds to. "Epitope" is also known as "antigenic determinant". Eptiope or antigenic determinant generally consists of chemically active surface groups of a molecule such as amino acids, carbohydrates or sugar side chains, and generally has a specific three-dimensional structure and a specific charge characteristic. For example, an epitope generally comprises at least 3, 4, 5, 6, 7, 8, 9, 10, 11, 12, 13, 14 or 15 consecutive or non-consecutive amino acids in a unique steric conformation, which may be "linear" or "conformational". See, for example, Epitope Mapping Protocols in Methods in Molecular Biology, Vol. 66, G. E. Morris, Ed. (1996). In a linear epitope, all the interaction sites between a protein and an interaction molecule (e.g., an antibody) are present linearly along the primary amino acid sequence of the protein. In a conformational epitope, the interaction sites span over amino acid residues that are separate from each other in a protein.

As used herein, the term "epitope peptide" refers to peptide fragment on antigen that acts as epitope. Under some conditions, epitope peptide alone can be specifically recognized/bound by an antibody against the epitope. Under some other conditions, epitope peptide has to be fused to a carrier protein to facilitate the epitope to be specifically recognized by an antibody. As used herein, the term "carrier protein" refers to such a protein that may act as a carrier of epitope peptide, i.e. the epitope peptide may be inserted into the protein at a specific position (for example, inner, N-terminal or C-terminal of the protein), so that the epitope peptide can be presented and thus can be recognized by an antibody or immune system. Such carrier proteins are well known by a person skilled in the art, including, for example, HPV L1 protein (into which the epitope peptide may be inserted between amino acids from positions 130 to 131 or amino acids from positions 426 to 427 of the protein, see Slupetzky, K. et al., Chimeric papillomavirus-like particles expressing a foreign epitope on capsid surface loops [J]. J Gen Virol, 2001, 82: 2799-2804; Varsani, A. et al., Chimeric human papillomavirus type 16 (HPV-16) L1 particles presenting the common neutralizing epitope for the L2 minor capsid protein of HPV-6 and HPV-16 [J]. J Virol, 2003, 77: 8386-8393), HBV core antigen (the amino acids from positions 79 to 81 of the protein may be replaced with the epitope peptide, see, Koletzki, D., et al. HBV core particles allow the insertion and surface exposure of the entire potentially protective region of Puumala hantavirus nucleocapsid protein [J]. Biol Chem, 1999, 380: 325-333), woodchuck hepatitis virus core protein (the amino acids from positions 79 to 81 of the protein may be replaced with the epitope peptide, see, Sabine König, Gertrud Beterams and Michael Nassal, *J. Virol.* 1998, 72(6):4997), and CRM197 protein (the epitope peptide may be linked to the N-terminal or C-terminal of the protein or a fragment thereof). Optionally, a linker (e.g., a flexible or rigid linker) may be used between an epitope peptide and a carrier protein to promote their foldings, respectively.

Antibodies may be screened depending on competitiveness of binding to the same epitope by conventional techniques known by a person skilled in the art. For example, study on competition or cross-competition may be conducted to obtain antibodies that compete or cross-compete with each other for binding to antigens (e.g. RSV fusion protein). High-throughput methods for obtaining antibodies binding to the same epitope, which are based on their cross-competition, are described in an international patent application WO 03/48731. Therefore, antibodies and antigen binding fragments (i.e. antigen binding portions) thereof, which compete with monoclonal antibodies according to the invention (e.g. monoclonal antibody 5C4) for binding to the same epitopes on RSV fusion protein, can be obtained by conventional techniques known by a person skilled in the art.

As used herein, the term "isolated" refers to a state obtained from natural state by artificial means. If a certain "isolated" substance or component is present in nature, it is possible because its natural environment changes, or the substance is isolated from natural environment, or both. For example, a certain unisolated polynucleotide or polypeptide naturally exists in a certain living animal body, and the same polynucleotide or polypeptide with a high purity isolated from such a natural state is called isolated polynucleotide or polypeptide. The term "isolated" excludes neither the mixed artificial or synthesized substance nor other unpure substances that do not affect the activity of the isolated substance.

As used herein, the term "*E. coli* expression system" refers to an expression system consisting of *E. coli* (strain) and a vector, wherein the *E. coli* (strain) are derived from the commercially available strains, including, but not limited to: GI698, ER2566, BL21 (DE3), B834 (DE3), and BLR (DE3).

As used herein, the term "vector" refers to a nucleic acid vehicle which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, artificial chromosome such as yeast artificial chromosome (YAC), bacterial artificial chromosome (BAC) or P1-derived artificial chromosome (PAC); phage such as λ phage or M13 phage and animal virus. The animal viruses that can be used as vectors, include, but are not limited to, retrovirus (including lentivirus), adenovirus, adeno-associated virus, herpes virus (such as herpes simplex virus), pox virus, baculovirus, papillomavirus, papova virus (such as SV40). A vector may comprises multiple elements for controlling expression, including, but not limited to, a promoter sequence, a transcription initiation sequence, an enhancer sequence, a selection element and a reporter gene. In addition, a vector may comprise origin of replication.

As used herein, the term "host cell" refers to a cell into which a vector can be introduced, including, but not limited to, prokaryotic cell such as *E. coli* or *Bacillus subtilis*, fungal cell such as yeast cell or *Aspergillus*, insect cell such as S2 *Drosophila* cell or Sf9, and animal cell such as fibroblast, CHO cell, COS cell, NSO cell, HeLa cell, BHK cell, HEK 293 cell or human cell.

As used herein, the term "identity" refers to the match degree between two polypeptides or between two nucleic acids. When two sequences for comparison have the same base or amino acid monomer sub-unit at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by using a computer program such as Align program (DNAstar, Inc.) which is based on the method of Needleman, et al. (J. Mol. Biol. 48:443-453, 1970). The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having alkaline side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, a corresponding amino acid residue is preferably substituted with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

As used herein, the term "immunogenicity" refers to ability of stimulating the formation of specific antibodies or sensitized lymphocytes in organisms. It not only refers to the property of an antigen to stimulate a specific immunocyte to activate, proliferate and differentiate so as to finally generate immunologic effector substance such as antibody and sensitized lymphocyte, but also refers to the specific immune response that antibody or sensitized T lymphocyte can be formed in immune system of an organism after stimulating the organism with an antigen. Immunogenicity is the most important property of an antigen. Whether an antigen can successfully induce the generation of an immune response in a host depends on three factors, properties of an antigen, reactivity of a host, and immunization means.

As used herein, the term "specifically bind" refers to the binding of two molecules in a non-random manner, such as the reaction between an antibody and the antigen it directs to. In some embodiments, an antibody that specifically binds to an antigen (or an antibody specific for an antigen) refers to an antibody that binds to the antigen with an affinity ($K_D$) of less than about $10^{-5}$ M, e.g. of less than about $10^{-6}$ M, $10^{-7}$ M, $10^{-8}$ M, $10^{-9}$ M or $10^{-10}$ M or less.

As used herein, the term "$K_D$" refers to a dissociation equilibrium constant of a specific antibody-antigen interaction, which is used to describe the binding affinity of an antibody to an antigen. The smaller the dissociation equilibrium constant is, the more closely the antibody binds to the antigen and the higher the affinity of the antibody to the antigen is. Generally, an antibody (e.g., the monoclonal antibody 5C4 according to the invention) binds to an antigen (e.g., RSV fusion protein) with a $K_D$ of less than about $10^{-5}$ M, e.g., less than about $10^{-6}$ M, $10^{-7}$ M, $10^{-8}$ M, $10^{-9}$ M or $10^{-10}$ M or less, determined by, for example, surface plasmon resonance (SPR) in BIACORE device.

As used herein, the term "monoclonal antibody" and the term "MAb" have the same meanings and are used interchangeably; the term "polyclonal antibody" and the term "PAb" have the same meanings and are used interchangeably; the term "polypeptide" and "protein" have the same meanings and are used interchangeably. Moreover, in the invention, amino acids are generally represented by single letter codes or three letter codes. For example, alanine may be represented by A or Ala.

As used herein, the term "hybridoma" and the term "hybridoma cell line" may be used interchangeably. When the term "hybridoma" and the term "hybridoma cell line" are mentioned, they also include subclone and progeny cell of hybridoma. For example, when hybridoma cell line RSV-Y-5C4-2 (also referred to as hybridoma cell line 5C4 for short) is mentioned, it also refers to the subclone and progeny cell of hybridoma cell line RSV-Y-5C4-2.

As used herein, the term "a pharmaceutically acceptable carrier and/or excipient" refers to a carrier and/or excipient pharmacologically and/or physiologically compatible with a subject and an active agent, which is well known in the art (see, e.g., Remington's Pharmaceutical Sciences. Edited by Gennaro A R, 19th ed. Pennsylvania: Mack Publishing Company, 1995), and includes, but is not limited to pH adjuster, surfactant, adjuvant and ionic strength enhancer. For example, the pH adjuster includes, but is not limited to, phosphate buffer; the surfactant includes, but is not limited to, cationic, anionic, or non-ionic surfactant, e.g., Tween-80; the ionic strength enhancer includes, but is not limited to, sodium chloride.

As used herein, the term "adjuvant" refers to a non-specific immunopotentiator, which can enhance immune response to an antigen or change the type of immune response in an organism when it is delivered together with the antigen to the organism or is delivered to the organism in advance. There are a variety of adjuvants, including, but not limited to, aluminium adjuvants (for example, aluminum hydroxide), Freund's adjuvants (for example, Freund's complete adjuvant and Freund's incomplete adjuvant), coryne bacterium parvum, lipopolysaccharide, cytokines, and the like. Freund's adjuvant is the most commonly used adjuvant in animal experiments now. Aluminum hydroxide adjuvant is more commonly used in clinical trials.

As used herein, the term "protein vaccine" refers to a polypeptide-based vaccine, optionally comprising an adjuvant. Polypeptides in vaccines may be obtained by genetic engineering techniques or by methods of chemical synthesis. As used herein, the term "nucleic acid vaccine" refers to a DNA or RNA-based vaccine (such as plasmid, e.g., expression plasmid), optionally comprising an adjuvant.

As used herein, the term "an effective amount" refers to an amount that is sufficient to achieve or at least partially achieve the expected effect. For example, an amount effective for preventing a disease (such as RSV infection or diseases associated with RSV infection) refers to an amount effective for preventing, suppressing, or delaying the occurrence of a disease (such as RSV infection or diseases associated with RSV infection). An effective amount for treating a disease refers to an amount effective for curing or at least partially blocking a disease and its complication in a patient having the disease. The determination of such an effective amount is within the ability of a person skilled in the art. For example, an amount effective for a therapeutic use depends on severity of a disease to be treated, general state of the immune system in a patient, general conditions of a patient, such as age, weight and gender, administration means of drugs, additional therapies used simultaneously, and the like.

As used herein, the biological function of the epitope peptide according to the invention includes, but is not limited to one or more of:

1) specific binding to antibody 5C4;

2) ability of reducing serum level of RSV fusion protein in a subject (optionally, after fusing the epitope peptide to a carrier protein);

3) ability of inducing an antibody response of effective clearance of RSV and RSV-infected cells in vivo (optionally, after fusing the epitope peptide to a carrier protein); and 4) ability of treating RSV infection or diseases associated with RSV infection (e.g., pneumania) in a subject (optionally, after fusing the epitope peptide to a carrier protein).

The inventor surprisingly found by conducting a lot of experimental researches that some epitopes of RSV fusion protein (e.g. the epitope comprised in the amino acids from positions 148 to 216 of RSV fusion protein, or the epitope comprising the amino acid residues from positions 62 to 69 and 196 to 209 of RSV fusion protein) and antibodies recognizing these epitopes promote the stabilization and maintenance of pre-F conformation of F-protein, and these epitopes and the stabilization and maintenance of pre-F conformation are of important significance for the induction of immune response in organisms, and said antibodies have an excellent biological activity (e.g. a very high neutralizing activity), and thus are very suitable for the prevention or treatment of RSV infection or diseases associated with RSV infection (e.g. pneumonia, such as infantile pneumonia).

Thus, in one aspect, the invention provides an isolated epitope peptide or a variant thereof, wherein the epitope peptide consists of amino acid residues from positions 148 to 216 of RSV fusion protein or a fragment thereof, and at least comprises amino acid residues from positions 196 to 209 of RSV fusion protein, and the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In a variety of embodiments according to the invention, preferably, the epitope peptide according to the invention is present with its steric conformation in pre-F protein, and the variant retains the steric conformation of the epitope peptide from which it originates.

In a preferred embodiment, the epitope peptide consists of amino acid residues from positions 196 to 209 of RSV fusion protein, and the variant differs from the epitope peptide from which it originates merely by conservative substitution of one or several (e.g., 1, 2, 3 or 4) amino acid residues and retains the biological function of the epitope peptide from which it originates.

In another preferred embodiment, the epitope peptide consists of amino acid residues from positions 196 to 216 of RSV fusion protein, and the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In another preferred embodiment, the epitope peptide consists of amino acid residues from positions 185 to 216 of RSV fusion protein, and the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In another preferred embodiment, the epitope peptide consists of amino acid residues from positions 185 to 216 of RSV fusion protein, wherein the amino acids from positions 185 to 194 form a β-sheet in the secondary structure of the protein, and the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In another preferred embodiment, the epitope peptide consists of amino acid residues from positions 176 to 216 of RSV fusion protein, and the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In another preferred embodiment, the epitope peptide consists of amino acid residues from positions 176 to 216 of RSV fusion protein, wherein the amino acids from positions 176 to 181 and the amino acid residues from positions 185 to 194 form a β-sheet in the secondary structure of the protein, and the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In another preferred embodiment, the epitope peptide consists of amino acid residues from positions 148 to 216 of RSV fusion protein, and the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In another preferred embodiment, the epitope peptide consists of amino acid residues from positions 148 to 216 of RSV fusion protein, wherein the amino acids from positions 176 to 181 and the amino acids from positions 185 to 194 form a β-sheet in the secondary structure of the protein, and the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In another aspect, the invention provides an isolated epitope peptide consisting of a first peptide and a second peptide, or a variant thereof, wherein the first peptide consists of amino acid residues from positions 148 to 216 of RSV fusion protein or a fragment thereof and at least comprises amino acid residues from positions 196 to 209 of RSV fusion protein, and the second peptide consists of amino acid residues from positions 62 to 69 or 62 to 76 of RSV fusion protein, wherein the variant differs from the epitope peptide from which it originates merely by conservative substitution of one or several (e.g., 1, 2, 3, 4, 5, 6, 7, 8 or 9) amino acid residues and retains the biological function of the epitope peptide from which it originates.

In a variety of embodiments according to the invention, preferably, the first peptide and the second peptide are present in their steric conformation in pre-F protein, and the variant retains the steric conformation of the epitope peptide from which it originates.

In a preferred embodiment, the first peptide and the second peptide together form a spatial structure present in pre-F conformation of RSV fusion protein.

In a further preferred embodiment, the first peptide consists of amino acid residues from positions 196 to 209 of RSV fusion protein. In another preferred embodiment, the first peptide consists of amino acid residues from positions 196 to 216 of RSV fusion protein. In another preferred embodiment, the first peptide consists of amino acid residues from positions 185 to 216 of RSV fusion protein. In another preferred embodiment, the first peptide consists of amino acid residues from positions 185 to 216 of RSV fusion protein, wherein the amino acids from positions 185 to 194 form a β-sheet in the secondary structure of the protein. In another preferred embodiment, the first peptide consists of amino acid residues from positions 176 to 216 of RSV fusion protein. In another preferred embodiment, the first peptide consists of amino acid residues from positions 176 to 216 of RSV fusion protein, wherein the amino acids from positions 176 to 181 and the amino acids from positions 185 to 194 form a β-sheet in the secondary structure of the protein. In another preferred embodiment, the first peptide consists of amino acid residues from positions 148 to 216 of RSV fusion protein. In another preferred embodiment, the first peptide consists of amino acid residues from positions 148 to 216 of RSV fusion protein, wherein the amino acids from positions 176 to 181 and the amino acids from positions 185 to 194 form a β-sheet in the secondary structure of the protein.

As known by a person skilled in the art, an epitope peptide or a variant thereof may be fused to a carrier protein to enhance the immunogenicity of the epitope peptide or variant thereof so that the epitope peptide or variant thereof can be recognized by immune system in organisms and induce an effective prevention of virus infection.

Therefore, in one aspect, the invention also provides a recombinant protein comprising the isolated epitope peptide or variant thereof according to the invention, and a carrier protein, wherein the recombinant protein is not a naturally occurring protein or a fragment thereof. In the recombinant protein, the epitope peptide or variant thereof may be linked to the N-terminus or C-terminus of the carrier protein, be inserted into the carrier protein, or be used to replace a portion of the amino acid sequence of the carrier protein, depending on the carrier protein used. In addition, optionally, the epitope peptide or variant thereof may be linked to the carrier protein via a linker (a rigid or flexible linker, e.g., $(GGGGS)_3$). The recombinant protein according to the invention may be produced by any method, for example, by genetic engineering method (recombinant technique), or by method of chemical synthesis.

In another aspect, the invention also provides an isolated nucleic acid molecule, comprising a nucleotide sequence encoding the epitope peptide or variant thereof according to the invention, or the recombinant protein according to the invention. In another aspect, the invention provides a vector comprising the isolated nucleic acid molecule as described above. The vector according to the invention may be a cloning vector, or an expression vector. In a preferred embodiment, the vector according to the invention may be, for example, plasmid, cosmid, phage, and the like. In a preferred embodiment, the vector can express the epitope peptide or variant thereof according to the invention or the recombinant protein according to the invention in a subject (for example, mammalian, e.g. human).

In another aspect, the invention also provides a host cell comprising the isolated nucleic acid molecule or vector according to the invention. Such host cells include, but are not limited to, prokaryotic cell such as *E. coli* cell, and eukaryotic cell such as yeast cell, insect cell, plant cell and animal cell (such as mammalian cell, e.g., mouse cell, human cell, etc.). The cell according to the invention may be a cell line, such as 293T cell.

In another aspect, the invention also provides a method for producing the recombinant protein according to the invention, comprising culturing the host cell according to the invention under suitable conditions, and recovering the recombinant protein according to the invention from the cell culture.

In another aspect, the invention provides a protein vaccine, comprising the epitope peptide (or a variant thereof) or the recombinant protein according to the invention, and a pharmaceutically acceptable carrier and/or excipient (e.g., adjuvant). In a preferred embodiment, the protein vaccine comprises one or more epitope peptides according to the invention, wherein said epitope peptides may be separate or tandem, modified or unmodified, coupled to another protein or not.

In another aspect, the invention provides a method for preventing, treating or inhibiting RSV infection or a disease associated with RSV infection (e.g. pneumonia, such as infantile pneumonia) in a subject, comprising administering a therapeutically effective amount of the epitope peptide (or a variant thereof) or the recombinant protein or the protein vaccine according to the invention to a subject in need thereof.

In another aspect, the invention provides use of the epitope peptide (or a variant thereof) or the recombinant protein according to the invention in the manufacture of a protein vaccine for preventing, treating or inhibiting RSV infection or a disease associated with RSV infection (e.g. pneumonia, such as infantile pneumonia) in a subject.

In another aspect, the invention provides the epitope peptide (or a variant thereof) or the recombinant protein according to the invention, for preventing, treating or inhibiting RSV infection or a disease associated with RSV infection (e.g., pneumonia, such as infantile pneumonia) in a subject.

In another aspect, the invention provides a gene vaccine comprising the isolated nucleic acid molecule or the vector according to the invention, and a pharmaceutically acceptable carrier and/or excipient (e.g., adjuvant). In a preferred embodiment, the gene vaccine comprises DNA or RNA. In such embodiments, the DNA or RNA may be naked or encapsulated into a shell having a delivery and/or protective function. In a further preferred embodiment, the shell may be shell of adenovirus, adeno-associated virus, lentivirus, retrovirus, etc., or may be another material that is synthesized by chemical methods and is capable of exerting a similar function.

In another aspect, the invention provides a method for preventing, treating or inhibiting RSV infection or a disease associated with RSV infection (e.g., pneumonia, such as infantile pneumonia) in a subject, comprising administering a therapeutically effective amount of the gene vaccine or the isolated nucleic acid molecule or the vector according to the invention to a subject in need thereof.

In another aspect, the invention provides use of the isolated nucleic acid molecule or the vector according to the invention in the manufacture of a gene vaccine for preventing, treating or inhibiting RSV infection or a disease associated with RSV infection (e.g., pneumonia, such as infantile pneumonia) in a subject.

In another aspect, the invention provides the isolated nucleic acid molecule or the vector according to the invention for preventing, treating or inhibiting RSV infection or a disease associated with RSV infection (e.g., pneumonia, such as infantile pneumonia) in a subject.

In another aspect, the invention provides a composition comprising the epitope peptide (or a variant thereof) or the recombinant protein, or the isolated nucleic acid molecule or the vector according to the invention, and a pharmaceutically acceptable carrier and/or excipient (e.g., adjuvant). In a preferred embodiment, the pharmaceutical composition comprises one or more epitope peptides according to the invention, wherein said epitope peptides may be separate or tandem, modified or unmodified, coupled to another protein or not.

In another aspect, the invention provides a method for producing an antibody capable of specifically binding and neutralizing RSV and stabilizing and maintaining the pre-F conformation of F protein, comprising 1) immunizing non-human animal (e.g., mouse) with the epitope peptide (or a variant thereof) or the recombinant protein according to the invention, so that antibodies are generated in the animal; and 2) screening antibodies that have neutralizing activity for RSV but are not reactive with post-F protein (i.e. do not bind to or substantively do not bind to post-F protein).

In another aspect, the invention provides an antibody or an antigen binding fragment thereof capable of specifically binding and neutralizing RSV and stabilizing and maintaining the pre-F conformation of F protein, produced by the method as described above.

In one aspect, the invention provides a monoclonal antibody and an antigen binding fragment thereof, wherein the monoclonal antibody can specifically bind to the epitope peptide according to the invention. Preferably, the monoclonal antibody can specifically bind to amino acid residues from positions 148 to 216 of RSV fusion protein or a fragment thereof (e.g., amino acid residues from positions 196 to 209 of RSV fusion protein), and/or amino acid residues from positions 62 to 69 or positions 62 to 76 of RSV fusion protein In a preferred embodiment, the monoclonal antibody or antigen binding fragment thereof is selected from Fab, Fab', $F(ab')_2$, Fd, Fv, dAb, complementary determining region fragment, single chain antibody (e.g., scFv), mouse antibody, rabbit antibody, humanized antibody, full-human antibody, chimeric antibody (e.g., human mouse chimeric antibody), or bispecific or poly-specific antibody.

In a preferred embodiment, the monoclonal antibody comprises non-CDR region, and the non-CDR region is from species other than murine species, e.g., is from human antibody.

In a preferred embodiment, the monoclonal antibody specifically binds to RSV, and has a neutralizing activity for the virus. In a preferred embodiment, the monoclonal antibody does not bind to or substantively does not bind to post-F protein, but binds and stabilizes pre-F protein.

In a preferred embodiment, the monoclonal antibody comprises the following CDRs:

1) a heavy chain CDR1 set forth in SEQ ID NO:20;
2) a heavy chain CDR2 set forth in SEQ ID NO:21;
3) a heavy chain CDR3 set forth in SEQ ID NO:22;
4) a light chain CDR1 set forth in SEQ ID NO:23;
5) a light chain CDR2 set forth in SEQ ID NO:24; and
6) a light chain CDR3 set forth in SEQ ID NO:25.

In a preferred embodiment, the monoclonal antibody comprises a) a heavy chain variable region set forth in SEQ ID NO:17; and
b) a light chain variable region set forth in SEQ ID NO:19.

In a preferred embodiment, the monoclonal antibody is derived from the monoclonal antibody selected from the following group, or is an antibody selected from the following group:

monoclonal antibody produced by hybridoma cell line 5C4, wherein hybridoma cell line 5C4 is deposited in China Center for Type Culture Collection (CCTCC), and has a deposition number of CCTCC NO: C2012147.

In another aspect, the invention provides a monoclonal antibody and an antigen binding fragment thereof, capable of blocking the binding of the epitope peptide according to the invention or pre-F protein to the antibody produced by the hybridoma cell line 5C4 by at least 50%, preferably at least 60%, preferably at least 70%, preferably at least 80%, preferably at least 90%, preferably at least 95% or preferably at least 99%, wherein the hybridoma cell line 5C4 is deposited in China Center for Type Culture Collection (CCTCC), and has a deposition number of CCTCC NO: C2012147.

The epitopes recognized by such antibodies are the same as or overlap sterically with the epitopes recognized by the monoclonal antibody 5C4, so that such antibodies can reduce the binding of the monoclonal antibody 5C4 to the epitope peptide according to the invention or pre-F protein by at least 50%, preferably at least 60%, preferably at least 70%, preferably at least 80%, preferably at least 90%, preferably at least 95% or preferably at least 99%.

The invention also provides an isolated nucleic acid molecule, encoding the monoclonal antibody or antigen binding fragment thereof according to the invention. Such nucleic acid molecules may be isolated from hybridoma cells, or may be obtained by genetic engineering recombinant technique or methods of chemical synthesis.

In one aspect, the invention provides an isolated nucleic acid molecule, comprising a nucleic acid sequence encoding the heavy chain variable region of the monoclonal antibody according to the invention.

In a preferred embodiment, the heavy chain variable region is set forth in SEQ ID NO:17. In another preferred embodiment, the nucleic acid molecule has a nucleotide sequence set forth in SEQ ID NO:16.

In another aspect, the invention provides an isolated nucleic acid molecule, comprising a nucleic acid sequence encoding the light chain variable region of the monoclonal antibody according to the invention.

In a preferred embodiment, the light chain variable region is set forth in SEQ ID NO:19. In another preferred embodiment, the nucleic acid molecule has the nucleotide sequence set forth in SEQ ID NO:18.

In another aspect, the invention provides a vector comprising the isolated nucleic acid molecule according to the invention. The vector according to the invention may be a cloning vector, or an expression vector.

In a preferred embodiment, the vector according to the invention is a plasmid, a cosmid, a phage, etc.

In another aspect, the invention also provides a host cell comprising the isolated nucleic acid molecule or vector according to the invention. Such host cells include, but are not limited to, prokaryotic cell such as *E. coli* cell, and eukaryotic cell such as yeast cell, insect cell, plant cell and animal cell (such as mammalian cell, e.g., mouse cell, human cell, etc.). The cell according to the invention may be a cell line, such as 293T cell.

In another aspect, the invention provides a method for producing the monoclonal antibody or antigen binding fragment thereof according to the invention, comprising culturing the host cell according to the invention under suitable conditions, and recovering the monoclonal antibody or antigen binding fragment thereof according to the invention from the cell culture.

In another aspect, the invention provides a hybridoma cell line 5C4, deposited in China Center for Type Culture Collection (CCTCC), with a deposition number of CCTCC NO: C2012147.

The amino acid sequences and/or nucleotide sequences of the heavy chain variable region, the light chain variable region, the heavy chain variable region CDRs and the light chain variable region CDRs can be determined from the monoclonal antibody 5C4 by conventional methods.

The amino acid sequences of the heavy chain variable region and the light chain variable region of the monoclonal antibody 5C4 are set forth in SEQ ID NO: 17 and 19, respectively; the nucleotide sequences encoding the same are set forth in SEQ ID NO: 16 and 18, respectively.

The amino acid sequences of the heavy chain variable region CDRs and the light chain variable region CDRs of the monoclonal antibody 5C4 are set forth in SEQ ID NO: 20-25, respectively.

In another aspect, the invention provides a kit comprising the monoclonal antibody or antigen binding fragment thereof according to the invention. In a preferred embodiment, the monoclonal antibody or antigen binding fragment thereof according to the invention further comprises a detectable marker. In a preferred embodiment, the kit further comprises a second antibody that specifically binds to the monoclonal antibody or antigen binding fragment thereof according to the invention. Preferably, the second antibody further comprises a detectable marker. The detectable marker is familiar to a person skilled in the art, including, but not limited to a radioisotope, a fluorescent substance, a luminescent substance, a chromophoric substance, an enzyme (e.g., horse radish peroxidase), and the like.

In another aspect, the invention provides a method for stabilizing pre-F protein, comprising using the monoclonal antibody or antigen binding fragment thereof according to the invention, or D25 or AM22 monoclonal antibody or antigen binding fragment thereof.

In another aspect, the invention provides a method for detecting the presence or level of pre-F protein in a sample, comprising using the monoclonal antibody or antigen binding fragment thereof according to the invention. In a preferred embodiment, the monoclonal antibody or antigen binding fragment thereof according to the invention further comprises a detectable marker. In another preferred embodiment, the method further comprises detecting the monoclonal antibody or antigen binding fragment thereof according to the invention by using a second antibody carrying a detectable marker. The method may be for diagnostic purpose or for non-diagnostic purpose (e.g., the sample is a cell sample, instead of a sample from a patient).

In another aspect, the invention provides a method for diagnosing whether a subject is infected with RSV, comprising: detecting the presence of RSV in an sample from the subject by using the monoclonal antibody or antigen binding fragment thereof according to the invention. In a preferred embodiment, the monoclonal antibody or antigen binding fragment thereof according to the invention further comprises a detectable marker. In another preferred embodiment, the method further comprises detecting the monoclonal antibody or antigen binding fragment thereof according to the invention by using a second antibody carrying a detectable marker.

In another aspect, the invention provides use of the monoclonal antibody or antigen binding fragment thereof according to the invention or D25 or AM22 monoclonal antibody or antigen binding fragment thereof in the manufacture of a kit for stabilizing pre-F protein, or detecting the presence or level of pre-F protein in a sample, or diagnosing whether a subject is infected by RSV.

In another aspect, the invention provides a pharmaceutical composition comprising the monoclonal antibody or antigen binding fragment thereof according to the invention, and a pharmaceutically acceptable carrier and/or excipient.

In another aspect, the invention provides a method for preventing or treating RSV infection or a disease associated with RSV infection (e.g., pneumonia, such as infantile pneumonia) in a subject, comprising administering a prophylactically or therapeutically effective amount of the monoclonal antibody or antigen binding fragment thereof according to the invention or the pharmaceutical composition according to the invention to a subject in need thereof.

In another aspect, the invention provides use of the monoclonal antibody or antigen binding fragment thereof according to the invention in the manufacture of a pharmaceutical composition for preventing or treating RSV infection or a disease associated with RSV infection (e.g., pneumonia, such as infantile pneumonia) in a subject.

In another aspect, the invention provides the monoclonal antibody or antigen binding fragment thereof according to the invention for preventing or treating RSV infection or a disease associated with RSV infection (e.g., pneumonia, such as infantile pneumonia) in a subject.

The vaccine (protein vaccine and gene vaccine), the medicament, and the pharmaceutical composition provided in the invention may be used alone or in combination, or can be used in combination with an additional pharmaceutically active agent (e.g., interferon drugs, such as interferon or PEGylated interferon).

In another aspect, the invention provides a method for expressing pre-F protein or an antigen-antibody complex, comprising co-expressing a nucleic acid encoding the monoclonal antibody or antigen binding fragment thereof according to the invention or D25 or AM22 monoclonal antibody or antigen binding fragment thereof, and a nucleic acid encoding F protein.

In another aspect, the invention provides a kit comprising a nucleic acid encoding the monoclonal antibody or antigen binding fragment thereof according to the invention or D25 or AM22 monoclonal antibody or antigen binding fragment thereof, and a nucleic acid encoding F protein.

Advantageous Effects of the Invention

The inventors discovered a new epitope of RSV fusion protein (F protein) for the first time, and surprisingly found that the new epitope and antibodies specifically recognizing the new epitope play an important role in the stabilization and maintenance of pre-F conformation of F protein.

In addition, the inventor also found that as compared to the antibodies against RSV fusion protein as known in the prior art, the antibodies of the invention, which specifically recognize the new epitope, have higher neutralizing activity, indicating that the pre-F conformation of F protein and the new epitope discovered in the invention play an important role in inducing an immune response against RSV.

Therefore, the epitope peptide according to the invention or the recombinant protein comprising the epitope peptide is effective as a protein vaccine for preventing RSV infection or diseases associated with RSV infection (e.g. infantile pneumonia) in a subject.

In addition, the monoclonal antibodies and antigen binding fragments thereof according to the invention have higher neutralizing activity, and thus can be used in a lower amount to effectively block infection of cells by RSV, and further can be used effectively in the prevention or treatment of RSV infection or diseases associated with RSV infection (e.g. infantile pneumonia) in a subject.

The embodiments of the invention are described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

Figure 15:
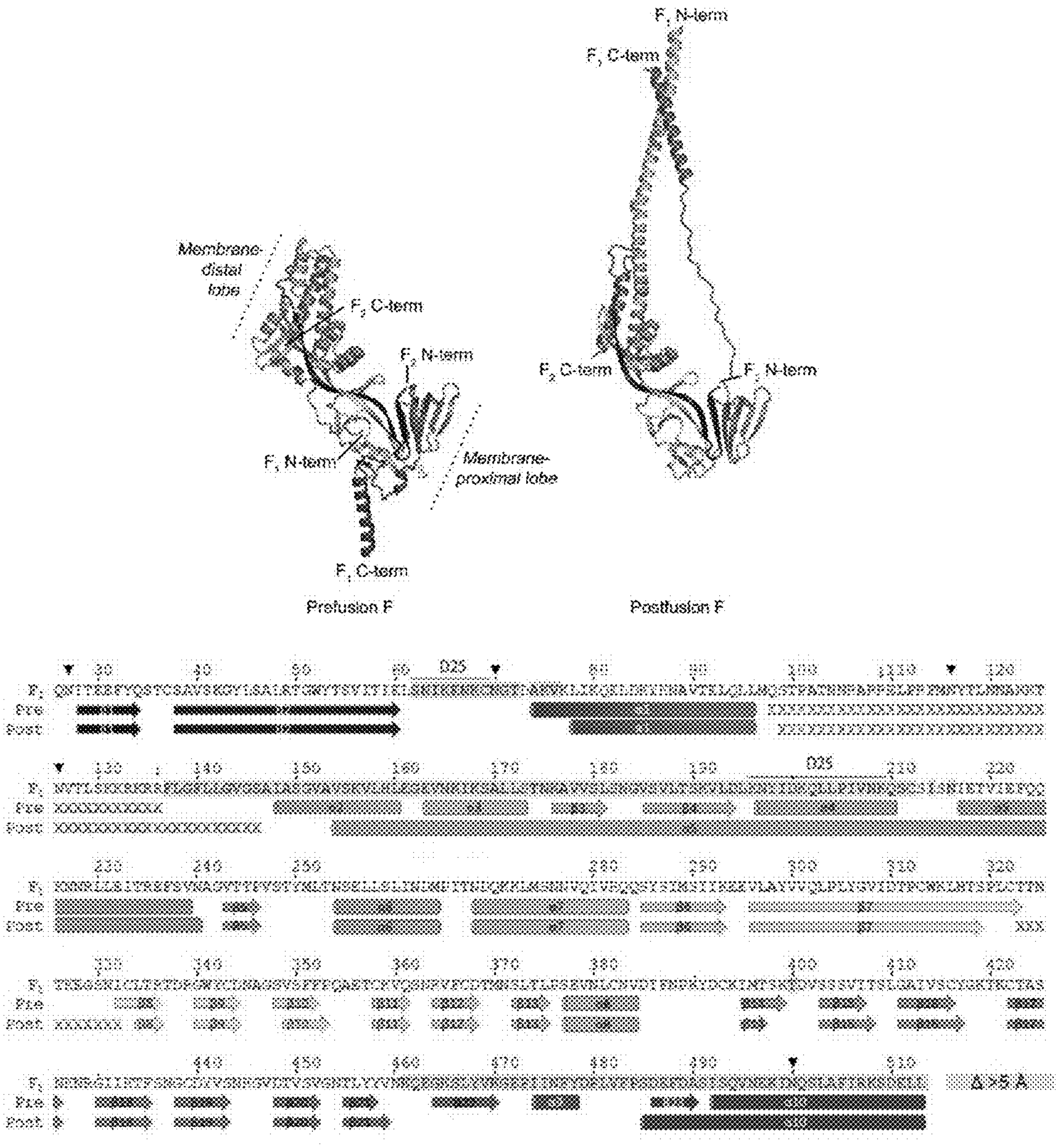
FIG. 15 shows the spatial structures of pre-F protein and post-F protein, and the corresponding amino acid sequences that constitutes the spatial structures, and the epitope sequence recognized by D25. The results show that there is a significant difference between the spatial structures of pre-F protein and post-F protein. Particularly, the spatial structure of pre-F protein includes α1-α10 helix and β1-β23 sheet; while the spatial structure of post-F protein includes al helix, α5-α8 helix, α10 helix, β1-β2 sheet and β5-β21 sheet.

In addition, the results in FIG. 15 also show that the core epitope of pre-F protein, recognized by D25 monoclonal antibody, is two peptide segments that are sterically close to each other, i.e. a.a. 62-69 and a.a. 196-209. The interacting interface of the two peptide segments shows that two segments (a.a.62-76 and a.a.137-216 (or more particularly, a.a.148-216)) of F protein or fragments thereof have an important effect on the recognition and stabilization of pre-F protein by such antibodies (the antibodies of the invention (e.g. 5C4), D25 and AM22), wherein two regions, a.a.176-181 and a.a.185-194, have a significant change between pre-F conformation and post-F conformation of F protein, i.e. they are in a conformation of β sheet (β3-β4 sheet) in pre-F protein, but are in a conformation of a helix (comprised in α5 helix) in post-F protein.

The information on sequences involved in the invention is provided in the following Table 1.

TABLE 1

Description of sequences

| SEQ ID NO: | Description of the sequence | Sequence information |
|---|---|---|
| 1 | amino acid sequence from positions 196 to 209 of F protein | KNYIDKQLLPIVNK |
| 2 | variant of the amino acid sequence from positions 196 to 209 of F protein | KNYINNQLLPIVNQ |
| 3 | amino acid sequence from positions 196 to 216 of F protein | KNYIDKQLLPIVNKQSCSISN |
| 4 | variant of the amino acid sequence from positions 196 to 216 of F protein | KNYINNQLLPIVNQQSCRISN |
| 5 | amino acid sequence from positions 185 to 216 of F protein | VSVLTSKVLDLKNYIDKQLLPIVNKQSCSISN |
| 6 | variant of the amino acid sequence from positions 185 to 216 of F protein | VSVLTSKVLDLKNYINNQLLPIVNQQSCRISN |
| 7 | amino acid sequence from positions 176 to 216 of F protein | KAVVSLSNGVSVLTSKVLDLKNYIDKQLLPIVNKQSCSISN |

TABLE 1-continued

Description of sequences

| SEQ ID NO: | Description of the sequence | Sequence information |
|---|---|---|
| 8 | variant of the amino acid sequence from positions 176 to 216 of F protein | KAVVSLSNGVSVLTSKVLDLKNYIN NQLLPIVNQQSCRISN |
| 9 | amino acid sequence from positions 148 to 216 of F protein | IASGIAVSKVLHLEGEVNKIKSALL STNKAVVSLSNGVSVLTSKVLDLKN YIDKQLLPIVNKQSCSISN |
| 10 | variant of the amino acid sequence from positions 148 to 216 of F protein | IASGIAVSKVLHLEGEVNKIKNALL STNKAVVSLSNGVSVLTSKVLDLKN YINNQLLPIVNQQSCRISN |
| 11 | amino acid sequence from positions 62 to 69 of F protein | SNIKENKC |
| 12 | variant of the amino acid sequence from positions 62 to 69 of F protein | SNIKETKC |
| 13 | amino acid sequence from positions 62 to 76 of F protein | SNIKENKCNGTDAKV |
| 14 | variant of the amino acid sequence from positions 62 to 76 of F protein | SNIKETKCNGTDTKV |
| 15 | amino acid sequence of F protein | MELLILKANAITTILTAVTFCFASG QNITEEFYQSTCSAVSKGYLSALRT GWYTSVITIELSNIKENKCNGTDAK VKLIKQELDKYKNAVTELQLLMQST PPTNNRARRELPRFMNYTLNNAKKT NVTLSKKRKRRFLGFLLGVGSAIAS GVAVSKVLHLEGEVNKIKSALLSTN KAVVSLSNGVSVLTSKVLDLKNYID KQLLPIVNKQSCSISNIETVIEFQQ KNNRLLEITREFSVNAGVTTPVSTY MLTNSELLSLINDMPITNDQKKLMS NNVQIVRQQSYSIMSIIKEEVLAYV VQLPLYGVIDTPCWKLHTSPLCTTN TKEGSNICLTRTDRGWYCDNAGSVS FFPQAETCKVQSNRVFCDTMNSLTL PSEINLCNVDIFNPKYDCKIMTSKT DVSSSVITSLGAIVSCYGKTKCTAS NKNRGIIKTFSNGCDYVSNKGMDTV SVGNTLYYVNKQEGKSLYVKGEPII NFYDPLVFPSDEFDASISQVNEKIN QSLAFIRKSDELLHNVNAGKSTTNI MITTIIIVIIVILLSLIAVGLLLYC KARSTPVTLSKDQLSGINNIAFSN |
| 16 | nucleotide sequence of 5C4 heavy chain variable region | GAGGTTCAGCTGCAGCAGTCTGGGG CAGAGCTTGTGAAGCCAGGGGCCTC AGTCAAGTTGTCCTGCACAGCTTCT GGCTTCAACATTAAAGACACCTTTT TTCACTGGGTGAAGCAGAGGCCTGA ACAGGGCCTGGAGTGGATTGGAAGG ATTGATCCTGCGGATGGTCATACTA AATATGACCCGAAGTTCCAGGGCAA GGCCACTATAACAGCAGACACATCC TCCAACACAGCCTTCCTGCAGCTCA GCAGCCTGACATCTGAGGACACTGC CGTCTATTACTGTGCTACTACTATT ACTGCGGTTGTACCTACCCCTTACA ATGCTATGGACTATTGGGGTCAAGG AACCTCAGTCACCGTCTCCTCAGCC AAAACAACAGCCCCACCTGTTTATC CATTGGCCCCTGG |
| 17 | amino acid sequence of 5C4 heavy chain variable region | EVQLQQSGAELVKPGASVKLSCTAS GFNIKDTFFHWKVQRPEQGLEWIGR IDPADGHTKYDPKFQGKATITADTS SNTAFLQLSSLTSEDTAVYYCATTI TAVVPTPYNAMDYWGQGTSVTVSSA KTTAPPVYPLAP |
| 18 | nucleotide sequence of 5C4 light chain variable region | GACATTGTGCTGACCCAATCTCCAG CTTCTTTGGCTGTGTCTCTAGGGCA GAGGACCACCATATCCTGCAGAGCC AGTGAAAGTGTTGATAGTTTTGACA ATAGTTTTATACACTGGTACCAGCA GAAACCAGGACAGCCACCCAAACTC CTCATCTTTCTTGCATCCAGCCTAG AATCTGGGGTCCCTGCCAGGTTCAG TGGCAGTGGGTCTAGGACTGACTTC ACCCTCACCATTGATCCTGTGGAGG CTGATGATGCTGCAACCTATTACTG TCAGCAAAGTAATGAGGATCCATTC ACGTTCGGCTCGGGGACAAAGTTGG AAATAAAACGGGCTGATGCTGCACC AACTGTATCCATCTTCCCACCATCC AGT |
| 19 | amino acid sequence of 5C4 light chain variable region | DIVLTQSPASLAVSLGQRTTISCRA SESVDSFDNSFIHWYQQKPGQPPKL LIFLASSLESGVPARFSGSGSRTDF TLTIDPVEADDAATYYCQQSNEDPF TFGSGTKLEIKRADAAPTVSIFPPS S |
| 20 | 5C4 heavy chain CDR1 | GFNIKDTF |
| 21 | 5C4 heavy chain CDR2 | IDPADGHT |
| 22 | 5C4 heavy chain CDR3 | ATTITAVVPTPYNAMDY |
| 23 | 5C4 light chain CDR1 | ESVDSFDNSF |
| 24 | 5C4 light chain CDR2 | LAS |
| 25 | 5C4 light chain CDR3 | QQSNEDPFT |
| 26 | MVhF-B1 | 5'-ATgRAATgSASCTgggTYWTYC TCTT-3' |
| 27 | MVhF-B2 | 5'-ATggACTCCAggCTCAATTTAg TTTTCCT-3' |
| 28 | MVhF-C1 | 5'-ATggCTgTCYTRgBgCTgYTCY TCTg-3' |
| 29 | MVhF-C2 | 5'-ATggVTTggSTgTggAMCTTgC YATTCCT-3' |
| 30 | MVhF-C3 | 5'-ATgAAATgCAgCTggRTYATST TCTT-3' |
| 31 | MVhF-D1 | 5'-ATggRCAgRCTTACWTYYTCAT TCCT-3' |
| 32 | MVhF-D2 | 5'-ATgATggTgTTAAgTCTTCTgT ACCT-3' |
| 33 | MVhF-D3 | 5'-ATgggATggAgCTRTATCATSY TCTT-3' |

TABLE 1-continued

Description of sequences

| SEQ ID NO: | Description of the sequence | Sequence information |
|---|---|---|
| 34 | MVhF-E1 | 5'-ATgAAgWTgTggBTRAACTgg RT-3' |
| 35 | MVhF-E2 | 5'-ATggRATggASCKKRTCTTTMT CT-3' |
| 36 | MVhF-E3 | 5'-ATgAACTTYgggYTSAgMTTgR TTT-3' |
| 37 | MVhF-F1 | 5'-ATgTACTTgggACTgAgCTgTg TAT-3' |
| 38 | MVhF-F2 | 5'-ATgAgAgTgCTgATTCTTTT gTg-3' |
| 39 | MVhF-F3 | 5'-ATggATTTTgggCTgATTTTTT TTATTg-3' |
| 40 | MVhR | 5'-CCAgggRCCARKggATARCANg RTgg-3' |
| 41 | MVkF-A | 5'-ATgRAgWCACAKWCYCAggTCT TT-3' |
| 42 | MVkF-B | 5'-ATggAgACAgACACACTCCTgC TAT-3' |
| 43 | MVkF-C | 5'-ATggAgWCAgACACACTSCTgY TATgggT-3' |
| 44 | MVkF-D1 | 5'-ATgAggRCCCCTgCTCAgWTTY TTggWTCTT-3' |
| 45 | MVkF-D2 | 5'-ATgggCWTCAAgATgRAgTCAC AKWYYCWgg-3' |
| 46 | MVkF-D3 | 5'-ATgAgTgTgCYCACTCAggTCC TggSgTT-3' |
| 47 | MVkF-E1 | 5'-ATgTggggAYCgKTTTYAMMCT TTTCAATTg-3' |
| 48 | MVkF-E2 | 5'-ATggAAgCCCCAgCTCAgCTTC TCTTCC-3' |
| 49 | MVkF-E3 | 5'-ATgAgMMKTCMTTCATTCYTg gg-3' |
| 50 | MVkF-F1 | 5'-ATgAKgTHCYCgCTCAgYTYC TRg-3' |
| 51 | MVkF-F2 | 5'-ATggTRTCCWCASCTCAgTTCC TTg-3' |
| 52 | MVkF-F3 | 5'-ATgTATATATgTTTgTTgTCTA TTTCT-3' |
| 53 | MVkF-F4 | 5'-ATgAAgTTgCCTgTTAggCTgT TggTgCT-3' |
| 54 | MVkF-G1 | 5'-ATggATTTWCARgTgCAgATTW TCAgCTT-3' |
| 55 | MVkF-G2 | 5'-ATggTYCTYATVTCCTTgCTgT TCTgg-3' |
| 56 | MVkF-G3 | 5'-ATggTYCTYATVTTRCTgCTgC TATgg-3' |
| 57 | MVkR | 5'-ACTggATggTgggAAgAT ggA-3' |

Description of Deposition of Biological Materials

Hybridoma cell line RSV-Y-5C4-2 of the invention, deposited in China Center for Type Culture Collection (CCTCC, Wuhan University, Wuhan, China) on Oct. 22, 2012, has an deposition number of CCTCC NO: C2012147.

Specific Modes for Carrying Out the Invention

The present invention is illustrated by reference to the following examples (which are used only for the purpose of illustration and are not intended to limit the protection scope of the present invention).

Unless indicated otherwise, the molecular biological experimental methods and immunological assays used in the present invention are carried out substantially in accordance with the methods as described in Sambrook J et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; restriction enzymes are used under the conditions recommended by manufacturers of the products. When the conditions are not specified in the Examples, the experiments are carried out according to the conventional conditions or the conditions recommented by the manufacturers. The reagents or devices used in the present invention, the manufacturers of which are not indicated, are conventional products in the art that are commercially available. Those skilled in the art understand that the examples are used for illustrating the present invention, but not intended to limit the protection scope of the present invention.

Example 1. Preparation of RSV Virus

Preparation and Amplification of RSV A2 Strain

RSV A2 strain was prepared and donated by NIH Dr. Barney S. Graham (Graham et al., 1988) laboratory.

Hep2 cells with a confluence rate of 80% were cultured at 37° C. for 6 h; the supernatant was removed; 1 ml RSV A2 strain was added, and incubated at room temperature for 1 h. 10% MEM medium was then added to a volume of 15 ml, and the culture was performed at 37° C. for 4 d. The cells and the cell supernatant were collected and transferred to a pre-cooled 50 ml centrifuge tube, and put in a refrigerated centrifuge and centrifuged at 1000 rpm, 4° C. for 15 min after being disrupted by a hand-grasp Ultrasonic Disrupter (50%, disruption for 1 s and stop for 3 s). The obtained supernatant was transferred to a pre-cooled 50 ml centrifuge tube, and then was subpackaged at 1 ml/tube, and quickly frozen in a dry ice-alcohol mixed liquid, and was finally stored at −80° C.

Preparation and Amplification of RSV GFP Virus

RSV GFP virus was prepared by NIH Dr. Peter Collins (Hallak et al.), and was donated by NIH Dr. Barney S. Graham laboratory.

Hep2 cells with a confluence rate of 80% were cultured at 37° C. for 6 h; the supernatant was removed; 1 ml RSV GFP virus was added, and incubated at room temperature for 1 h. 10% MEM medium was then added to a volume of 15 ml, and the culture was performed at 37° C. for 4 d. The cells and the cell supernatant were collected and transferred to a pre-cooled 50 ml centrifuge tube, and put in a refrigerated centrifuge and centrifuged at 1000 rpm, 4° C. for 15 min after being disrupted by a hand-grasp Ultrasonic Disrupter (50%, disruption for 1 s and stop for 3 s). The obtained supernatant was transferred to a pre-cooled 50 ml centrifuge tube, and then was subpackaged at 1 ml/tube, and quickly frozen in a dry ice-alcohol mixed liquid, and was finally stored at −80° C.

Example 2. Expression of Post-F Protein and Construction of DNA-F Vector

Expression of Post-F Protein

The sequence of post-F protein was from RSV-A2 virus. In order to enhance the expression of post-F protein, the amino acids at positions 102 (P102), 379 (1379) and 447 (M447) of its amino acid sequence were substituted with alanine (P102A), valine (1379V) and valine (M447V), respectively. In addition, the fusion peptide fragment of positions 137-146 was removed from the sequence of post-F protein. The condon-optimized post-F sequence was inserted into an eukaryotic expression vector pLEXm (synthesized by Regensburg Company), thereby obtaining a post-F expression plasmid pLEXm-postF, which contained a site recognized by HRV 3C protease and 8×His tag at its C terminus. pLEXm-postF was transformed into HEK293F cells (purchased from Invitrogen Company) via a transient transfection system (TrueFect-Max, purchased from United BioSystems Company). The transformed cells were subjected to suspension culture in a shaking table at 120 rpm, 9% $CO_2$, 37° C. for 4-5 d. The cells were collected, and the protein was firstly purified by Ni2+-NTA Resin (purchased from Qiagen Company), wherein the elution buffer was 20 mM Tris-HCl pH 7.5, 200 mM NaCl and 250 mM imidazole, pH 8.0; and then further purified by StrepTactin resin (purchased from Novagen Company) according to the instructions. The purified protein was cleaved by HRV 3C protease (Novagen), and then passed through Ni2+-NTA again to remove the uncleaved protein and the affinity tag. The protein was then purified by passing through Superdex 200 column (purchased from GE Healthcare Company), wherein the buffer was 2 mM Tris-HCl pH 7.5, 150 mM NaCl and 0.02% NaN3, and then the protein was finally concentrated to about 6 mg/mL.

Construction of DNA-F

The fragment of interest (full-length F protein of RSV) was constructed into a shuttle plasmid ptrack-CMV, to obtain a plamisd pAdTrack-CMV-RSV F. The plamisd was linearized by Pmel single enzyme cleavage at 37° C. for more than 7 h, and the system for enzyme cleavage was 50 uL. The buffer and phosphatase were added to the tube, and the reaction was performed at 37° C. for more than 7 h. Then, ethanol precipitation was performed, and the product after centrifugation was re-suspended in sterile water. BJAdEasy competent cells were transfected (so that pAdTrack-CMV-RSV F and pAdEasy-1 are recombined in *E. coli* BJ5183), and then were coated to LB plate comprising kanamycin, and cultured at 37° C. 6-8 small bacterial colonies were picked up, and the plasmid therein was extracted, and the size of the plasmid was identified (the adenoviral plasmid pAdEasy-1 was of 33414 bp). Identification was carried out by Pacl enzyme cleavage: two fragments were obtained by the cleavage, one was of about 30 kb, and the other was of 3.0 kb or 4.5 kb. The positive recon, which was identified to be correct, was transferred to *E. coli* DH5α; the bacteria were stored, and were extracted to obtain the plasmid with a high copy number for further use. 1-2 flasks of 29335 cells ($2*10^6$ cells per flask) were cultured for 24 h. Pacl was used to digest 4 ug of the recombinant adenoviral plasmid. The plasmid was precipitated with ethanol, and was re-suspended in 20 uL sterile water. 4 ug Pacl-digested plasmid and 20 uL Lipofectamine (GIBCO BRL) were mixed in 500 uL OptiMem I medium (for one flask of cells), and were incubated at room temperature for 15-30 min. The cells were washed with 4 mL serum-free medium once. 2.5 mL OptiMem I was added to each flask. The cells were incubated at 37° C. for about 10 min. The Lipofectamine-DNA mixed liquid was added to the cell flask, and was incubated at 37° C. 4 h later, the supernatant comprising the Lipofectamine-DNA mixed liquid was sucked out, 6 mL fresh complete medium was added, and the culture was incubated at 37° C. overnight. 7-10 d after transfection, the cells were scratched off by using a rubber scraper (instead of trypsin), and then was transferred to a 50 mL conical tube. After centrifugation, 2 mL HBSS or sterile PBS was used for re-suspension of the cells. The cells were frozen in dry ice/methanol bath, thawed at 37° C. in water bath, and vigorously shaken. The process of "freezing/thawing/shaking" was repeated for 3 times, and the product was stored at −20° C. 293β5 cells were transfected with said virus suspension, and the culture was incubated at 37° C. for 48 h until the fluorescence was very strong. The infected cells were detached by pipetting the medium and then centrifuged at 3000 rpm for 3 min. The precipitate was re-suspended, and was subjected to freezing-thawing in liquid nitrogen for 6 times (until the cells were lysed) and then centifuged at 4000 rpm for 30 min, and the supernatant was kept. To a super centrifuge tube, 5 ml 40% Cscl, 4.5 ml 15% Cscl were added, and then the supernatant was added, the mixture was left for laminating. After a balanced state was achieved, super centrifugation was performed at 4° C., 32000 rpm for 16 h, resulting in two bands. The thick band located at the bottom was carefully sucked out. After dialysis in 5% sucrose, 20 mM TB8.0 of $MgCl_2$, the purified recombinant adenovirus was obtained.

Example 3. Preparation of Monoclonal Antibodies

Preparation of Hybridoma:

DNA immunization method by tail intravenous injection and PEG-fusion method were used to obtain monoclonal antibodies. For detail, please refer to Ed Harlow et al., "Antibodies A Laboratory Manual", Cold Spring Harbor Laboratory 1988. The process in brief was as followed.

Immunization of mice: A plasmid comprising full-length F gene of RSV was used for initial immunization. Prior to immunization, PBS was mixed and emulsified with an equivalent volume of Freund's adjuvant (CFA). The mice were multi-point injected via muscles of arms and legs, 300 ul for each mouse and each time. The plasmid comprising full-length F gene of RSV was diluted with PBS to a concentration of 50 ug/ml, 2 ml was administered to each mouse via tail vein by hydrodynamic injection. 10 d and 17 d after the initial immunization, the mice were subjected to booster immunization by using the same dose of PBS plus freund incomplete adjuvant (IFA), respectively. To each mouse, 2 ml adenovirus containing $10^6$ copies of full-length F gene of RSV was then injected. After the second booster, blood was collected for determining the inhibitory titer of HI. When the titer reached 1:640, the spleen of mice was taken for fusion. A booster immunization was carried out again 72 hr before the fusion, wherein RSV-A2 virus liquid was injected via spleen once, at 50 ul/each mouse. 15 fusion plates were prepared.

Fusion: the spleen cells from the mouse for which the antibodies in serum had a highest titer for neutralizing RSV GFP, were fused with mouse myeloma cells SP2/0. The spleen was grounded to obtain a suspension of spleen cells, and then was mixed with mouse myeloma cells SP2/0, the number of which was ten times lower and which were in exponential growth phase. Under the action of PEG1500 for 1 min, the two kinds of cells were fused together. The liquid of fusion cells (100 ml) was then subpackaged to 10 96-well plates, for culturing. The fusion medium is a RPMI1640 complete screening medium containing HAT and 20% FBS. Antigen specific clones were screened by indirect ELISA and neutralization test. Monoclonal antibody cell lines having neutralizing activity and no post-F reactivity were screened. After coloning for three times, stable monoclonal antibody cell lines were obtained.

Screening of hybridomas: after culturing the fused cells in 96-well plates for 10 days, the supernatant was taken for RSV-post F enzyme-linked immunosorbent assay and RSV-A2 neutralization test, enzyme-linked immunosorbent assay or RSV-A2 positive wells were used for further coloning, until the antibodies secreted by the cell line could stably block RSV-A2 and was not reactive with post F.

Screening result: one hybridoma cell line RSV-Y-5C4-2 was obtained, wherein the monoclonal antibody 5C4 secreted thereby has no reactivity with post-F, and had a high neutralizing activity.

Culturing of hybridoma: the stable hybridoma cell line was firstly subjected to amplification culture in a $CO_2$ incubator, and was transferred from a 96-well plate to a 24-well plate, and later to a 50 ml cell flask for amplification culture. The cells collected from the cell flask were injected to peritoneal cavity of mice, and 7-10 d later, ascites were absorbed from the peritoneal cavity of mice.

Purification of monoclonal antibodies: the ascites was subjected to precipitation with 50% ammonium sulfate, and then was subjected to dialysis in PB, pH7.4, and to HPLC purification through DEAE column, to obtain purified monoclonal antibodies. The purity of the purified monoclonal antibody was identified by SDS-PAGE.

Example 4. Characterization of the Monoclonal Antibody 5C4

ELISA Assay for Determining Reactivity with Post-F

Figure 1:
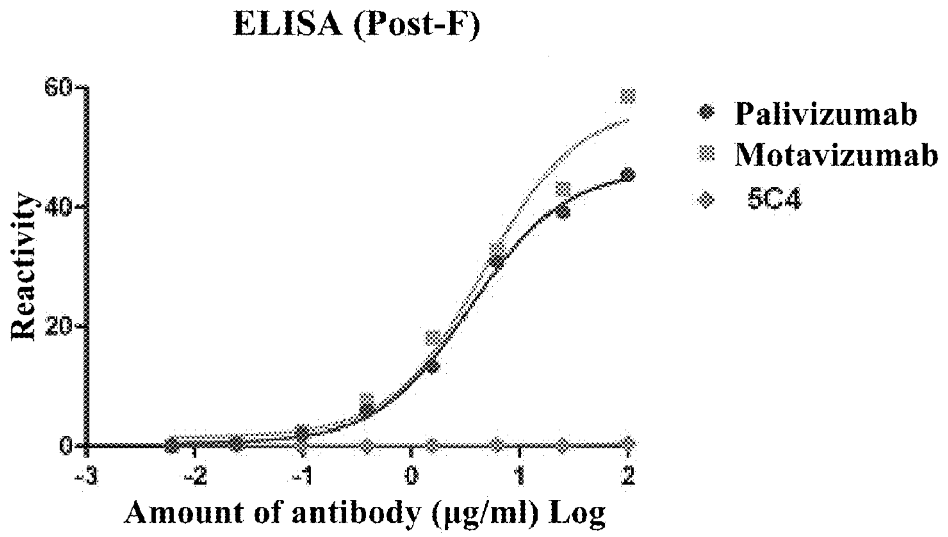
FIG. 1 shows the ELISA assay for determining the reactivity between 5C4 monoclonal antibody and post-F. The results show that as compared to the commercially available palivizumab (Synagis) and Motavizumab, 5C4 antibody has no significant reactivity with post-F.

Post-F was diluted with 1×CB to a concentration of 20 ng/100 μL, and was used for coating microwells of a polystyrene plate (100 μL per well), at 37° C. for 2 h. The plate was washed with PBST once. 180 μL PBS containing 2% (mass/volume) BSA was added for blocking, and the incubation was performed at 37° C. for 2 h. The antibodies to be tested were diluted to a concentration of 1 μg/ml as an initial titer, and 100 μL was added, and was subjected to 10-fold gradient dilution. Horseradish peroxidase (HPR)-labeled Goat Anti-Mouse was diluted by 1:5000, and was added at 100 μL as the secondary antibody for detection. When the value read in ELISA was greater than 0.5, it was detected as positive. The results were shown in FIG. 1. The results of FIG. 1 showed that 5C4 monoclonal antibody had almost no binding to post-F. As compared to the commercially available palivizumab (Synagis) and Motavizumab, 5C4 antibody had no significant reactivity with post-F.

Assay for Determining the Neutralizing Activity

Figure 2:
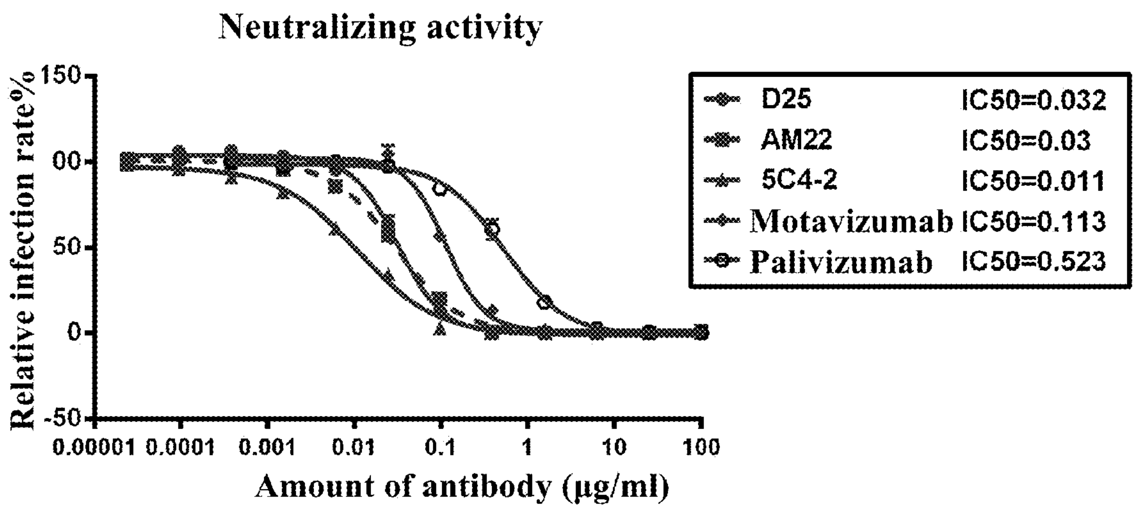
FIG. 2 shows the assay for determining the neutralizing activity of 5C4 monoclonal antibody. The results show that 5C4 monoclonal antibody has a higher neutralizing activity for RSV. In particular, as compared to the commercially available palivizumab (Synagis) and Motavizumab, as well as the previously reported antibody D25 (see the U.S. patent application Ser. No. 12/600,950) and AM22 (see the U.S. patent application Ser. No. 12/898,325), 5C4 monoclonal antibody has a higher neutralizing activity for RSV.

The antibodies to be tested were diluted to 100 μg/ml as an initial titer, and 100 μL was added to a U-shapted plate, and was subjected to 4-fold dilution. 75 μL $1\times10^6$ PFU RSV suspension was added, and was incubated at 37° C. for 1 h. 100 ul mixed solution after incubation was then added to a 96-well plate plated with 100 ul Hep2 cells, and incubated at 37° C. for 24 h. Paradim was used to determine the neutralizing activity. The results were shown in FIG. 2. The results of FIG. 2 showed that 5C4 monoclonal antibody had a strong neutralizing activity for RSV. Particularly, as compared to the commercially available palivizumab (Synagis) and Motavizumab, as well as the previously reported antibody D25 (see the U.S. patent application Ser. No. 12/600,950) and AM22 (see the U.S. patent application Ser. No. 12/898,325), 5C4 monoclonal antibody had a stronger neutralizing activity for RSV.

Assay for Determining Binding-Inhibitory Activity

Preparation of cells: Hep2 cells at $5\times10^4$ cells/100 μL were plated on each well of a 96-well plate, and were incubated at 37° C. for 2 h. The plate was then placed in 4° C. and cooled for 1 h.

Preparation of samples: 10 μL 1 mg/ml monoclonal antibody sample was added to 90 μL MEM medium, and then was subjected to 4-fold dilution with MEM medium to obtain 11 gradients. 75 μL virus sample was mixed with 75 μL diluted monoclonal antibody sample, and incubated at 25° C. for 1 h. The mixture was subsequently cooled to 4° C. 100 μL monoclonal antibody-virus mixture was added to Hep2 cells, and incubated at 4° C. for 1 h.

Figure 3:
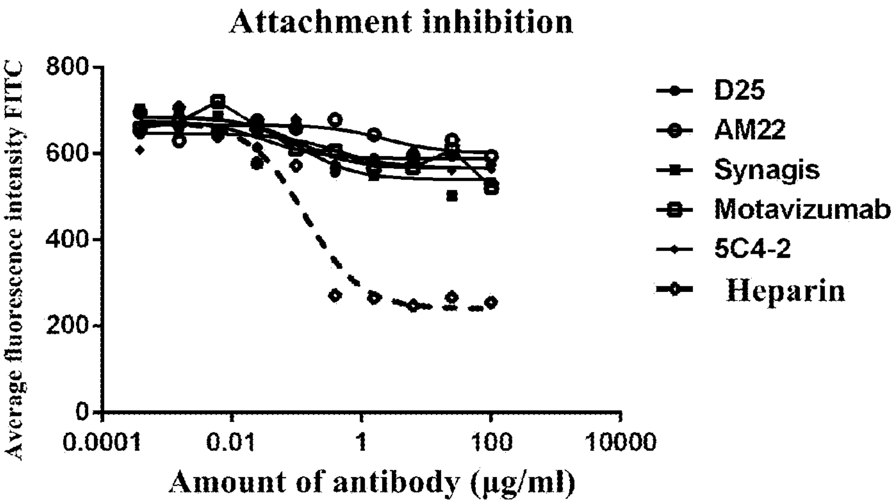
FIG. 3 shows the assay for determining the attachment inhibition of 5C4 monoclonal antibody. The results show that none of the tested monoclonal antibodies influences the attachment of viruses to cells.

Detection of samples: the supernatant was removed, and 100 μL pre-cooled PBS was added to wash cells. The cells were centrifuged at 4° C. 1700 G for 5 min, for twice. Then, 100 μL FITC-labeled goat anti-RSV antibody (1:1000 diluted, purchased from Biodesign International Company) was added, and incubated at 4° C. for 45 min. The supernatant was removed, and 100 μL pre-cooled PBS was added to wash cells. The cells were centrifuged at 4° C. 1700 G for 5 min. After removing the supernatant, 150 μL 0.5% paraformaldehyde was added to each well to fix cells. Finally, flow cytometer was used for detection. The results were shown in FIG. 3.

Assay for Determining Fusion-Inhibitory Activity

Preparation of cells: Hep2 cells at $5\times10^4$ cells/100 μL were plated on each well of a 96-well plate, and were incubated at 37° C. for 2 h. The plate was then placed at 4° C. and cooled for 1 h.

Preparation of samples: 10 μL 1 mg/ml monoclonal antibody sample was added to 90 μL MEM medium, and then was subjected to 4-fold dilution with MEM medium to obtain 11 gradients. The sample was placed at 4° C. for further use. RSV-GFP was 8-fold diluted with MEM medium. 50 μL RSV-GFP was added to cells, and incubated at 4° C. for 1 h. The supernatant was removed, and 50 μL pre-cooled PBS was added to wash cells. The cells were centrifuged at 4° C. 1700 G for 5 min, for three times. Then, 50 μL pre-cooled MEM medium was added to cells, and 50 μL diluted monoclonal antibody sample was also added to cells. The mixture was incubated at 4° C. for 1 hr. The cells were subsequently transferred to an environment at 37° C. for incubation for a period of 18 hr.

Figure 4:
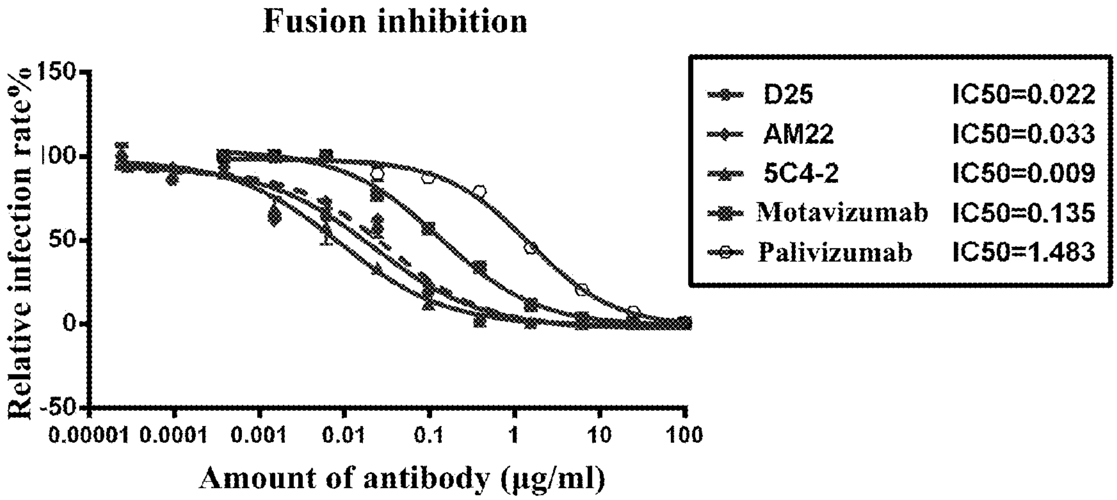
FIG. 4 shows the assay for determining the fusion inhibition activity of 5C4 monoclonal antibody. The results show that as compared to the commercially available palivizumab (Synagis) and Motavizumab, as well as the previously reported antibody D25 (see the U.S. patent application Ser. No. 12/600,950) and AM22 (see the U.S. patent application Ser. No. 12/898,325), 5C4 antibody has a stronger fusion-inhibitory activity.

Detection of samples: the supernatant was removed, and 100 μL pre-cooled PBS was added to wash cells. The cells were centrifuged at 4° C. 1700 G for 5 min, for twice. 150 μL 0.5% paraformaldehyde was added to each well to fix cells. Finally, flow cytometer was used for detection. The results were shown in FIG. 4. The results showed that as compared to the commercially available palivizumab (Synagis) and Motavizumab, as well as the previously reported antibody D25 (see the U.S. patent application Ser. No. 12/600,950) and AM22 (see the U.S. patent application Ser. No. 12/898,325), 5C4 antibody had a stronger fusion-inhibitory activity.

Assay for Determining the Capability to Capture Virus

Figure 5:
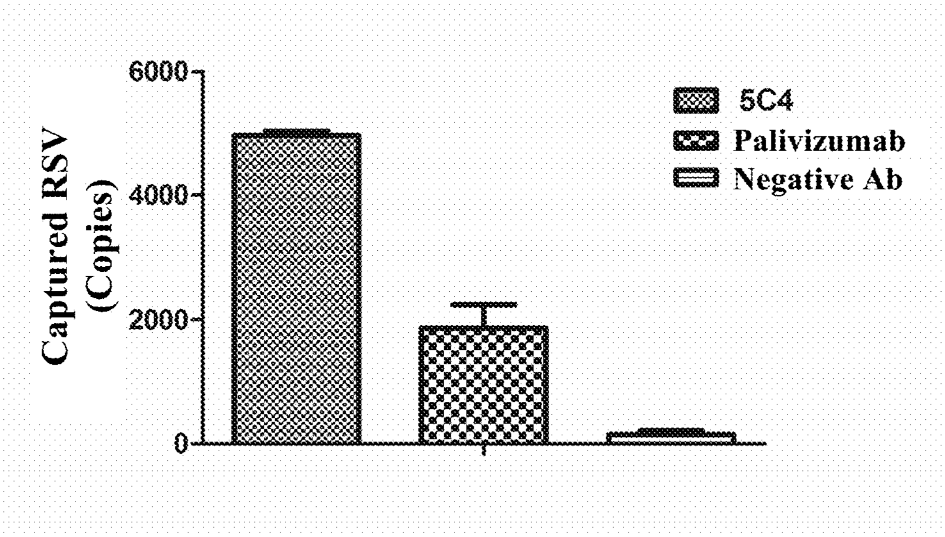
FIG. 5 shows the assay for determining the capability of 5C4 monoclonal antibody to capture viruses. The results show that 5C4 monoclonal antibody could specifically bind to RSV. In particular, as compared to the commercially available palivizumab (Synagis), 5C4 antibody has a stronger capability to capture RSV.

The monoclonal antibodies were diluted with 20 mM PB, pH 7.4 to a concentration of 3 μg/100 μL, and were used for coating microwells of a polystyrene plate, at 300 μL per well, at 4° C. for 10 h and then at 37° C. for 1 h. The plate was washed with PBST once. 350 μL PBS containing 2% (w/v) BSA was added for blocking, and the incubation was performed at 37° C. for 2 h. 200 μL $1\times10^6$ PFU RSV suspension was added, and was incubated at 37° C. for 2 h. After incubation, the plate was washed for five times. After the plate was washed, to each well, 200 μL Trizol was added for lysis. After lysis at 4° C. for 10 min, RNA of the RSV in the sample was extracted, and was subjected to quantitative Real-time PCR assay. The results were shown in FIG. 5. The results of FIG. 5 showed that the binding of 5C4 monoclonal antibody to RSV is very specific. As compared to the commercially available palivizumab (Synagis), 5C4 antibody had a stronger capability to capture RSV.

Figure 6:
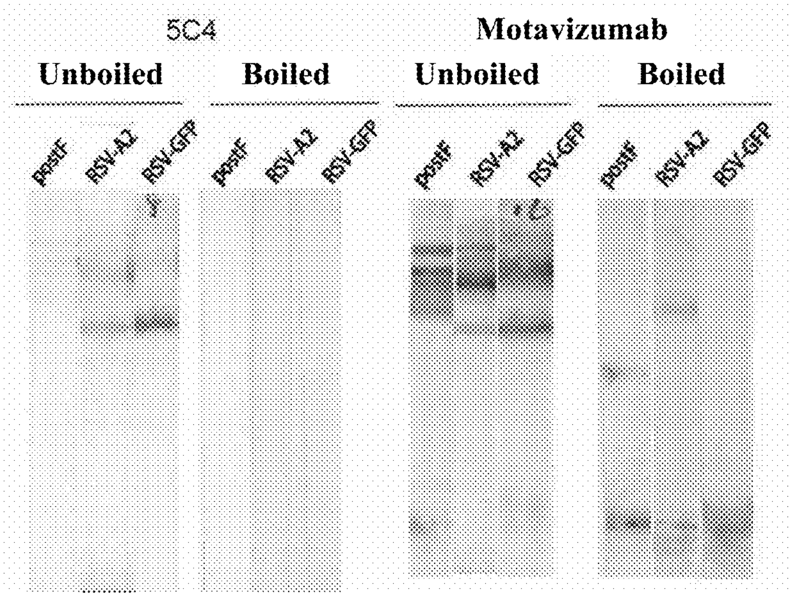
FIG. 6 shows the Western Blot assay for determining the reactivity of 5C4 monoclonal antibody. The results show that 5C4 monoclonal antibody is a monoclonal antibody that recognizes a conformational epitope, and recognizes non-denatured RSV-A2 and RSV-GFP, but does not recognize denatured RSV-A2 and RSV-GFP. In addition, 5C4 monoclonal antibody can specifically recognize RSV-A2 and RSV-GFP, but is not reactive to post-F substantively.

Western Blot assay for determining reactivity of 5C4 monoclonal antibody 10 ul boiled and non-boiled post-F, RSV-A2, RSV-GFP were loaded onto 10% SDS-polyacrylamide gel for electrophoresis, respectively, and then transmembrane was performed at 35 mA electric current for 1 h. After transmembrane, 5% skimmed milk was added and the blocking was performed at 4° C. overnight. The membrane was washed with TNT for three times, each for 10 min. The antibody to be tested, which was 1:2000 diluted with 1×TN, was added to the membrane. The incubation was performed in a shaking table at room temperature for 1 h. The membrane was washed with TNT for three times, each for 10 min. 1:5000 diluted horseradish peroxidase (HPR)-labeled Goat-Anti-Mouse antibody was added as the secondary antibody for detecting 5C4. 1:2000 diluted horseradish peroxidase (HPR)-labeled Mouse-Anti-human was added as the secondary antibody for detecting Motavizumab. The incubation was performed in a shaking table at room temperature for 1 h. The membrane was washed with TNT for three times, each for 10 min. Color was developed and photos were taken. The results were shown in FIG. 6. The results of FIG. 6 showed that 5C4 monoclonal antibody was a monoclonal antibody that recognizes a conformational epitope, and recognizes non-denatured RSV-A2 and RSV-GFP, but does not recognize denatured RSV-A2 and RSV-GFP. In addition, 5C4 monoclonal antibody could specifically recognize RSV-A2 and RSV-GFP, but is not reactive to post-F substantively.

Immunofluorescent Assay

Preparation of cells: Hep2 cells at $1\times10^5$ cells/mL were added to a 24-well plate plated with a slide, and were incubated at 37° C. for 4 h. The plate was then placed at 4° C. and cooled for 1 h.

Preparation of samples: the supernatant of cell culture was removed, and 100 μL pre-cooled RSV-A2 (RSV-A2 was 5-time diluted with MEM medium) was added and incubated at 4° C. for 1 h, and then the supernatant was removed. 1 ml MEM medium was added. The samples were taken for detection at 5 min, 1 h, 6 h, 16 h and 24 h, respectively.

Figure 7:
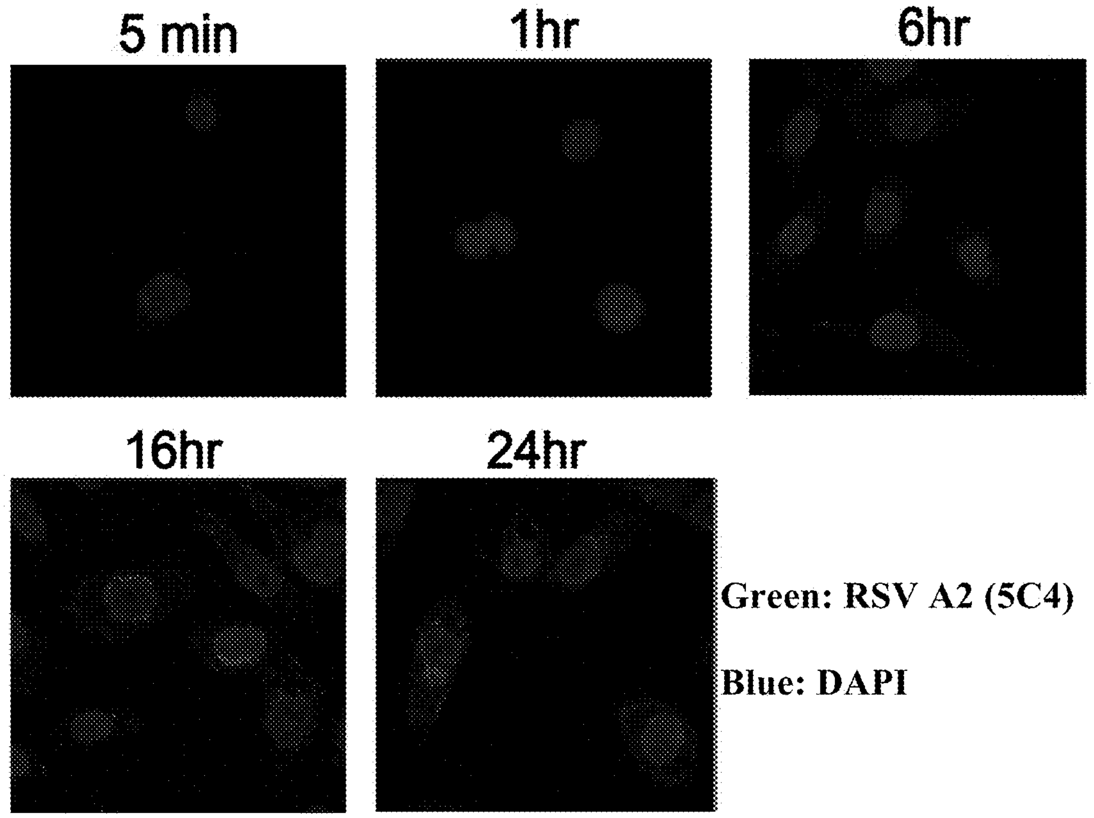
FIG. 7 shows the immunofluorescent assay using 5C4 monoclonal antibody. The results show that 5C4 monoclonal antibody is useful for detecting infection of cells by RSV A2.

Detection of samples: 1 ml pre-cooled PBS was added, the mixture was placed in a shaking table for 5 min, and the supernatant was removed. The process was repeated twice. 100 μL 0.4% paraformaldehyde was then added, and the mixture was incubated in dark at room temperature for 15 min. 1 ml PBS was added, and the mixture was placed in a shaking table for 5 min, and the supernatant was removed. The process was repeated for three times. 100 μL 0.3% TritonX-100 was added, and the mixture was incubated at room temperature for 10 min. 1 ml PBS was added, the mixture was placed in a shaking table for 5 min, and the supernatant was removed. The process was repeated for three times. 100 μL goat serum was then added, and the mixture was incubated at room temperature for 30 min. 1 ml PBS was added, the mixture was placed in a shaking table for 5 min, and the supernatant was removed. The process was repeated for three times. 100 μL monoclonal antibody sample (10-fold diluted with PBS) was added, and the mixture was incubated at room temperature for 3 h. 1 ml PBS was then added, the mixture was placed in a shaking table for 5 min, and the supernatant was removed. The process was repeated for three times. 100 μL FITC-labeled goat-anti-mouse polyclonal antibody (1:600, purchased from Sigma Company) was then added, and the mixture was incubated at room temperature for 30 min. 1 ml PBS was added, the mixture was placed in a shaking table for 5 min, and the supernatant was removed. The process was repeated for three times. 100 μL DAPI (1:2000, purchased from Invitrogen Company) was then added. After incubation at room temperature in dark for 5 min, 1 ml PBS was added, the mixture was placed in a shaking table for 5 min, and the supernatant was removed. The process was repeated for three times. Finally, the slide was taken out, and was placed on a glass slide carrying a mounting solution. Nail enamel was used for mounting, and laser scanning confocal microscope was used for observation. The results were shown in FIG. 7. The results of FIG. 7 showed that 5C4 monoclonal antibody was useful for detecting infection of cells with RSV A2.

Determination of the sequences of heavy chain and light chain variable region/CDRs of 5C4 monoclonal antibody The hybridoma cell line RSV-Y-5C4-2 that secreted 5C4 monoclonal antibody6, was amplified to $10^8$/ml, and the cells were suspended by blowing the semi-attached cells with a blow pipe. 1 ml cell suspension was centrifuged at 1000 rpm for 5 min, and the supernatant was removed. 1 ml PBS (PH7.44) was added to resuspend and wash cells, then the cells were centrifuged at 1000 rpm for 5 min, and the supernatant was removed. The process was repeated for three times. 800 μL Trizol (Roche Germany) was added to the cell precipitate, the mixture was shaken vigorously, and then standed for 10 min, to lyse the sample. 200 μL DEPC water was then added to supplement the water phase. 250 μL $CHCl_3$ was added to the sample, the mixture was shaken vigorously for 10 sec, and then was centrifuged at 12000 rpm, 4° C. for 5 min. 500-600 μL supernatant water phase was transferred to a new 1.5 ml EP tube, and 600 μL pre-cooled isopropanol (the ratio of isopropanol:supernatant by volume is about 1:1) was added, the mixture was subjected to reverse mixing gently, standed at 4° C. for 10 min, and then was centrifuged at 4° C. 12000 rpm for 10 min. The supernatant was sucked out, and the white precipitate was left. 700 μL 75% ethanol was added to the precipitate, and the mixture was centrifuged at 4° C. 12000 rpm for 5 min. The supernatant was sucked out, and was pumped with a pumping apparatus or baked until the white precipitate turned transparent. To the precipitate, 20 μL DEPC water was added to dissolve mRNA, and the mixture was subpacked into two tubes. To each tube, 1 ul reverse transcription primers were added, wherein the reverse transcription primer added to one tube, was MVkR (5'-ACT ggA Tgg Tgg gAA gAT ggA-3'), for amplifying the gene of the light chain variable region; the reverse transcription primer added to the other tube, was MVhR (5'-CCA ggg RCC ARK ggA TAR CAN gRT gg-3'), for amplifying the gene of the heavy chain variable region. Then, 1 ul dNTP was added to each tube, and the tubes were placed in a 72° C. water bath for 10 min and then immediately in an ice bath for 5 min. 10 ul 5× reverse transcription buffer, 1 ul AMV (10 u/ul, Pormega), and 1 ul Rnasin (40 u/ul, Promega) were then added. After mixing the mixture well, reverse transcription was carried out at 42° C., thereby reverse transcription of RNA into cDNA.

The gene of the antibody variable region was isolated by polymerase chain reaction (PCR) method. The combination of upstream primers for heavy chain variable region (Table 2), and the combination of upstream primers for light chain variable region (Table 3) were synthesized. In addition, MVkR was used as the downstream primer for amplification of the gene of light chain variable region, and MVhR was used as the downstream primer for amplification of the gene of heavy chain variable region. PCR templates are the two cDNAs as synthezied above. PCR conditions were: 94° C. 5 min; (94° C. 40 s, 53° C. 1 min, 72° C. 50 s)×35 cycles; 72° C. 15 min. The amplification products were recovered and were cloned to pMD 18-T vector, and then were sent to ShangHai Boya Company for sequencing. The sequences of the variable regions and CDRs of the antibody are shown in Tables 4-5, wherein the sequences of complementary determinant regions (CDRs) are determined by Kabat method (Kabat E A, Wu T T, Perry H M, Gottesman K S, Coeller K. Sequences of proteins of immunological interest, U.S Department of Health and Human Services, PHS, NIH, Bethesda, 1991).

TABLE 2

Sequences of upstream primers for amplification of heavy chain variable region gene of monoclonal antibody

| Upstream primer name | Upstream primer sequence |
|---|---|
| MVhF-B1 | 5'-ATgRAATgSASCTgggTYWTYCTCTT-3' |
| MVhF-B2 | 5'-ATggACTCCAggCTCAATTTAgTTTTCCT-3' |
| MVhF-C1 | 5'-ATggCTgTCYTRgBgCTgYTCYTCTg-3' |
| MVhF-C2 | 5'-ATggVTTggSTgTggAMCTTgCYATTCCT-3' |
| MVhF-C3 | 5'-ATgAAATgCAgCTggRTYATSTTCTT-3' |
| MVhF-D1 | 5'-ATggRCAgRCTTACWTYYTCATTCCT-3' |
| MVhF-D2 | 5'-ATgATggTgTTAAgTCTTCTgTACCT-3' |
| MVhF-D3 | 5'-ATgggATggAgCTRTATCATSYTCTT-3' |
| MVhF-E1 | 5'-ATgAAgWTgTggBTRAACTggRT-3' |
| MVhF-E2 | 5'-ATggRATggASCKKRTCTTTMTCT-3' |
| MVhF-E3 | 5'-ATgAACTTYgggYTSAgMTTgRTTT-3' |
| MVhF-F1 | 5'-ATgTACTTgggACTgAgCTgTgTAT-3' |
| MVhF-F2 | 5'-ATgAgAgTgCTgATTCTTTTgTg-3' |
| MVhF-F3 | 5'-ATggATTTTgggCTgATTTTTTTTATTg-3' |

TABLE 3

Sequences of upstream primers for amplification of light chain variable region gene of monoclonal antibody

| Upstream primer name | Upstream primer sequence |
|---|---|
| MVkF-A | 5'-ATgRAgWCACAKWCYCAggTCTTT-3' |
| MVkF-B | 5'-ATggAgACAgACACACTCCTgCTAT-3' |

TABLE 3-continued

Sequences of upstream primers for amplification of light chain variable region gene of monoclonal antibody

| Upstream primer name | Upstream primer sequence |
|---|---|
| MVkF-C | 5'-ATggAgWCAgACACACTSCTgYTATgggT-3' |
| MVkF-D1 | 5'-ATgAggRCCCCTgCTCAgWTTYTTggWTCTT-3' |
| MVkF-D2 | 5'-ATgggCWTCAAgATgRAgTCACAKWYYCWgg-3' |
| MVkF-D3 | 5'-ATgAgTgTgCYCACTCAggTCCTggSgTT-3' |
| MVkF-E1 | 5'-ATgTggggAYCgKTTTYAMMCTTTTCAATTg-3' |
| MVkF-E2 | 5'-ATggAAgCCCCAgCTCAgCTTCTCTTCC-3' |
| MVkF-E3 | 5'-ATgAgMMKTCMTTCATTCYTggg-3' |
| MVkF-F1 | 5'-ATgAKgTHCYCgCTCAgYTYCTRg-3' |
| MVkF-F2 | 5'-ATggTRTCCWCASCTCAgTTCCTTg-3' |
| MVkF-F3 | 5'-ATgTATATATgTTTgTTgTCTATTTCT-3' |
| MVkF-F4 | 5'-ATgAAgTTgCCTgTTAggCTgTTggTgCT-3' |
| MVkF-G1 | 5'-ATggATTTWCARgTgCAgATTWTCAgCTT-3' |
| MVkF-G2 | 5'-ATggTYCTYATVTCCTTgCTgTTCTgg-3' |
| MVkF-G3 | 5'-ATggTYCTYATVTTRCTgCTgCTATgg-3' |

TABLE 4

The nucleotide and amino acid sequences of heavy chain and light chain variable regions of monoclonal antibody

| Sequence name | Sequence No. |
|---|---|
| Vh nucleotide sequence | SEQ ID NO: 16 |
| Vh amino acid sequence | SEQ ID NO: 17 |
| Vk nucleotide sequence | SEQ ID NO: 18 |
| Vk amino acid sequence | SEQ ID NO: 19 |

TABLE 5

CDR sequences of Monoclonal antibody identified by Kabat method

| | | amino acid sequence | Sequence No. |
|---|---|---|---|
| heavy chain (Vh) | CDR1 | GFNIKDTF | SEQ ID NO: 20 |
| | CDR2 | IDPADGHT | SEQ ID NO: 21 |
| | CDR3 | ATTITAVVPTPYNAMDY | SEQ ID NO: 22 |
| light chain (Vk) | CDR1 | ESVDSFDNSF | SEQ ID NO: 23 |
| | CDR2 | LAS | SEQ ID NO: 24 |
| | CDR3 | QQSNEDPFT | SEQ ID NO: 25 |

Vκ refers to kappa chain variable region, which is one type of light chain variable region (VL).

Figure 8:
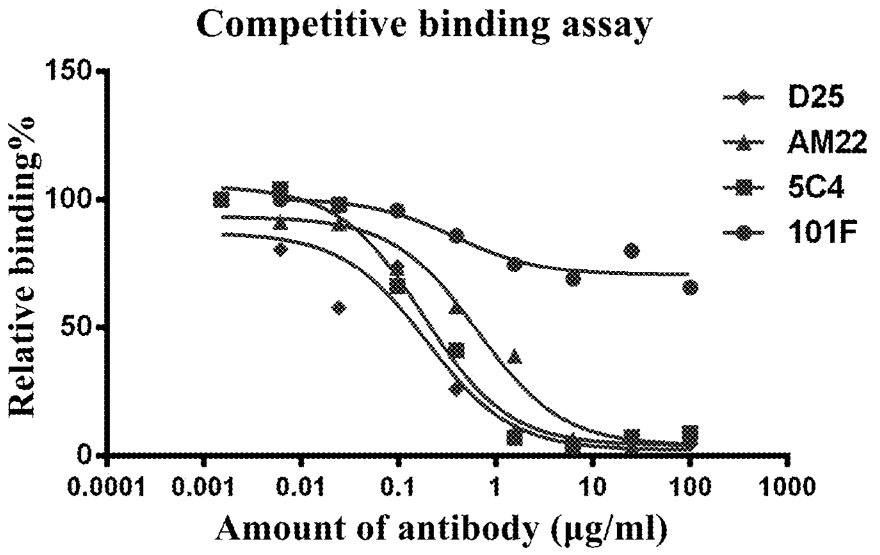
FIG. 8 shows the assay for determining the competitive binding of 5C4 monoclonal antibody with other monoclonal antibodies. The results show that there is competitive binding among AM22 monoclonal antibody, D25 monoclonal antibody and 5C4 monoclonal antibody, 5C4 monoclonal antibody may block the binding of AM22 monoclonal antibody or D25 monoclonal antibody by up to 99%. This indicates that 5C4 monoclonal antibody recognizes the same epitope as AM22 monoclonal antibody and D25 monoclonal antibody.

Example 5. Assay for Determining the Competitive Binding of 5C4 Monoclonal Antibody with Other Monoclonal Antibodies Competitive binding of antibodies was carried out with RSV infected HEp-2 cells. HEp-2 cells were infected with RSV in an amount three times of the infective dose for 18-20 h, and after infection, cell dissociation method was employed (a cell stripper, Mediatech Inc., Herndon, Va.) for cell isolation, and the cells were washed with PBS. Finally, the cells were suspended in PBS and incubated at $5\times10^4$ cells per well in a U-bottomed 96 well plate. The monoclonal antibodies 5C4, AM22, D25 and 101F (see McLellan et al., (2010), J Vriol, 84:12236-12244) at an initial dilution concentration of 100 μg/ml were added to HEp-2 cells. Half an hour later, 100 ul Alexa 488 and 1 μg/ml D25 complex were added, and the mixture was incubated at 4° C. for 1 h. The cells after incubation were washed with PBS for the first time, and then were filled with 0.5% paraformaldehyde. The product, resulted from the binding of D25 and Alexa 488 to the cells, was detected by flow cytometry (LSR II instrument, Becton Dickinson, San Jose, Calif.), the detected data was analyzed by FlowJo software version 8.5 (Tree Star, San Carlos, Calif.). The results were shown in FIG. 8. The results of FIG. 8 showed that there was competitive binding among AM22, D25 and 5C4, and 5C4 may block the binding of AM22 or D25 by up to 99%. This indicated that 5C4 monoclonal antibody recognized the same epitope on the antigen (F protein) as AM22 monoclonal antibody and D25 monoclonal antibody do.

Example 6. Analysis of Antigen-Antibody Complexes

Preparation of Antigen-Antibody Complexes

RSV F protein was derived from RSV A2 strain (accession P03420), and included three naturally occurring amino acid mutations (P102A, I379V and M447V). A mammalian codon-optimized gene encoding RSV F residues 1 to 513 with a C-terminus T4 fibritin trimerization motif was synthesized and subcloned into a mammalian expression vector pLEXm, and the vector also carried thrombin site, His-tag, and Streptagll. The plasmids expressing RSV F protein, D25 light chain and D25 heavy chain (with or without stop codon in the hinge region) were simultaneously transfected into suspended HEK293 GnTI cells. Alternatively, just the RSV F plasmid was transfected, with purified D25 Fab added to the HEK293 GnTI cells 3 hours post-transfection. After 4-5 days, the cell supernatant was collected, centrifuged, filtrated and concentrated. The obtained cell supernatant was firstly purified via $Ni^{2+}$-NTA resin (Qiagen, Valencia, Calif.) using an elution buffer consisting of 20 mM Tris-HCl pH7.5, 200 mM NaCl, 250 mM imidazole pH 8.0. Then, the product was concentrated and further purified over StrepTactin resin as per the manufacturer's instructions (Novagen, Darmstadt, Germany). His tag and streptocin tag were removed by treatment with thrombin protease overnight. An excessive amount of D25 antibody Fab was added, and then the mixture was purified on a Superose6 gel filtration column (GE Healthcare) with a running buffer of 2 mM Tris-HCl pH 7.5, 350 mM NaCl, and 0.02% $NaN_3$. The eluted complex was diluted with an equal volume of water and then was concentrated to a concentration of about 5 mg/ml. The same method was used to express and purify antigen-antibody complexes of AM22/F protein or 5C4/F protein.

Analysis of Electron Microscopy of Complexes

The samples were absorbed to freshly glow-discharged carbon-coated grids, rinsed shortly with water, and stained with freshly prepared 0.75% uranyl formate. Images were collected by FEI T20 microscope with an Eagle CCD camera. Image analysis and 2D average was carried out by using Bsoft (J. Struct. Biol. 157, 3(2007)) and EMAN (J. Struct. Biol. 128, 82(1999)). The results were shown in FIG. 9. The results showed that antigen-antibody complexes AM22/F protein, 5C4/F protein and D25/F protein had the same structure. This indicated that AM22 monoclonal antibody, 5C4 monoclonal antibody and D25 monoclonal antibody bind to the same epitope of F protein, and bind to F protein in the same conformation (pre-F conformation).

Further, electron microscopic results of antigen-antibody complexes palivizumab/F protein and 5C4/F protein were compared. The results were shown in FIG. 10, wherein the left figure showed the electron microscopic results of a complex of post-F and palivizumab; the bottom left figure showed the structure of the post-F in the white box of the top left figure, as observed under electron microscope; the right figure showed the electron microscopic results of a complex of pre-F and 5C4, the white box in the right figure showed the structure of the pre-F as observed under electron microscope. The results show that antigen-antibody complexes palivizumab/F protein and 5C4/F protein have significantly different structures, and the conformation of F protein is also significantly different between the two antigen-antibody complexes, wherein F protein is in post-F conformation in the palivizumab/F protein complex, while F protein is in pre-F conformation in the 5C4/F protein complex.

Figure 9:
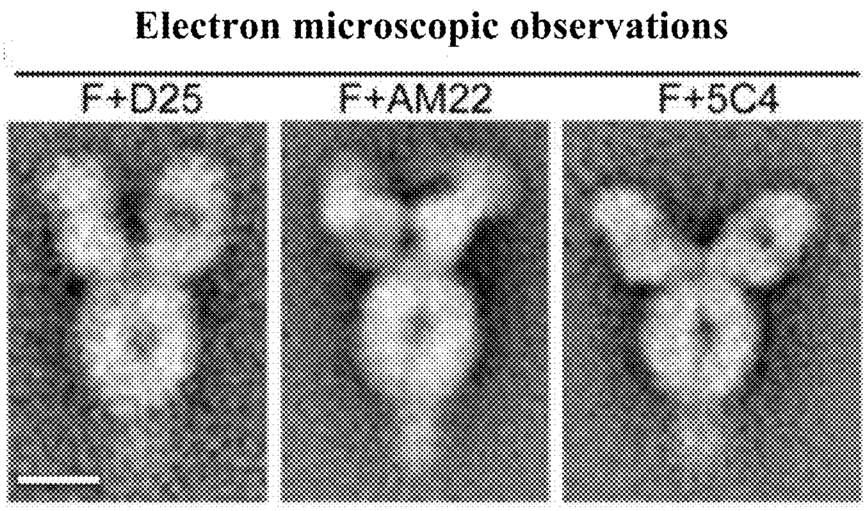
FIG. 9 shows the electron microscopic observations of antigen-antibody complexes AM22/F protein, 5C4/F protein and D25/Fprotein. The results show that antigen-antibody complexes AM22/F protein, 5C4/F protein and D25/F protein have the same structure. This indicates that AM22 monoclonal antibody, 5C4 monoclonal antibody and D25 monoclonal antibody bind to the same epitope of F protein, and bind to F protein in the same conformation (pre-F conformation).
Figure 10:
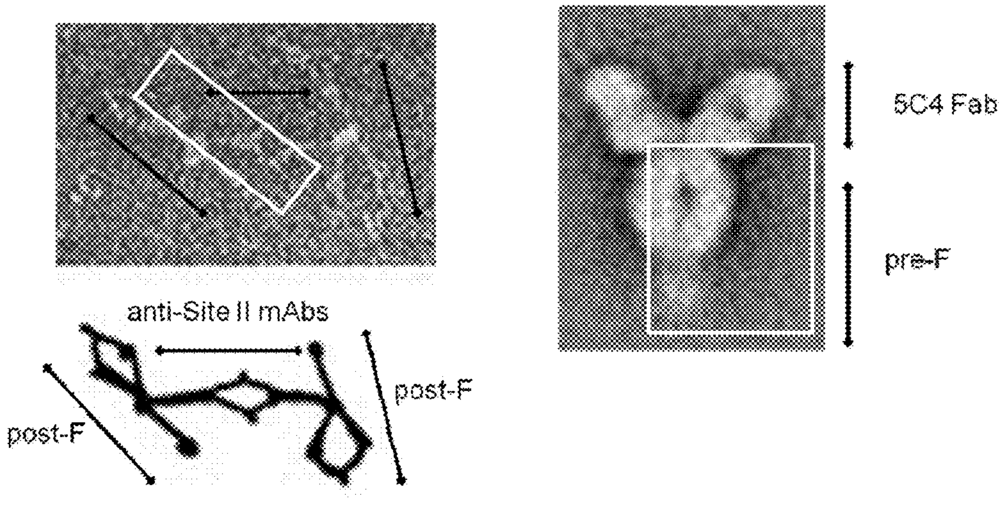
FIG. 10 shows the comparison of electron microscopic results of antigen-antibody complexs palivizumab/F protein and 5C4/F protein, wherein the left figure shows the electron microscopic results of a complex of post-F and palivizumab; the bottom left figure shows the structure of the post-F in the white box of the top left figure, as observed under electron microscope; the right figure shows the electron microscopic results of a complex of pre-F and 5C4; the white box in the right figure shows the structure of the pre-F, as observed under electron microscope. The results show that antigen-antibody complexes palivizumab/F protein and 5C4/F protein have significantly different structures, and the conformation of F protein is also significantly different in the two antigen-antibody complexes, wherein F protein is in post-F conformation in the palivizumab/F protein complex, while F protein is pre-F conformation in the 5C4/F protein complex.

The results in FIGS. 9 and 10 show that the epitope of F protein and the antibodies recognizing the epitope play an important role in stabilizing and maintaining pre-F conformation of F protein.

Crystallization of the Complexes

The initial crystals were cultured by the vapor diffusion method. At 20° C., the complex was mixed with 0.1 ul reservoir solution (40% (w/v) PEG 400, 5% (w/v) PEG 3350, and 0.1 M sodium acetate, pH 5.5) (54). The crystals were reproduced in hanging drops, and the crystal that diffracted to 3.6 Å was grown using a reservoir solution containing 30% (w/v) PEG 400, 3.75% (w/v) PEG 3350, 0.1 M HEPES pH 7.5, and 1% (v/v) 1,2-butanediol. The crystal was directly frozen in liquid nitrogen. The X-ray diffraction data were obtained by SER-CAT light beam ID-22, at a wavelength of 1.00 Å.

Diffraction and Deconstruction of the Complex Crystals

X-ray diffraction data were integrated and scaled with HKL200 (Z. Otwinowski, W. Minor, in Methods Enzymol. (Academic Press, 1997), vol. 276, pp. 307-326), and a molecular replacement solution was obtained by PHASER (A. J. McCoy et al., Phaser crystallographic software. J. Appl. Crystallogr. 40, 658(2007)), using the unbond D25 Fab structure and the residues aa 29-42, 49-60, 78-98, 219-306, 313-322, 333-343 and 376-459 from the post-F structure of RSV F protein (PDB ID: 3RRR, (J. Virol., 85, 7788 (2011)) as search models. Six sites from a NaAuCl4 derivative mapped to reactive side chains (F residues Met97/His159, Met264/Met274, His317, and Met396; D25 heavy chain residues Met19/His81 and His 58). Manual model building was carried out using COOT (Acta Crystallogr D Biol Crystallogr, 66, 486 (2010)), with secondary structure elements being established first. Refinement of individual sites, TLS parameters, and individual B-factors was performed in PHENIX (Acta Crystallogr D Biol Crystallogr 66, 213 (2010)), using unbond D25 Fab structure and the post-F structure as reference models during refinement. All RSV F residues in mature protein were established, except for the residues from $F_2$ C terminus to Met97. The final data collection and refinement statistics were summarized in Table 6. The crystal structures of the complexes were shown in FIGS. 11-13.

TABLE 6

| Data on crystal structures | | |
|---|---|---|
| | D25 Fab | D25 Fab + RSV F |
| PDB ID | 4JHA | 4JHW |
| Data collection | | |
| Space group | P6122 | P213 |
| Cell constants | | |
| a, b, c (Å) | 108.7, 108.7, 139.9 | 152.3, 152.3, 152.3 |
| α, β, γ(°) | 90.0, 90.0, 120.0 | 90.0, 90.0, 90.0 |
| Wavelength (Å) | 1.00 | 1.00 |
| Resolution (Å) | 50.0-1.6 (1.63-1.60) | 50.0-3.6 (3.73-3.60) |
| Rmerge | 11.2 (68.0) | 12.7 (81.4) |
| I/δI | 27.3 (2.1) | 16.4 (2.0) |
| Completeness (%) | 98.3 (86.1) | 99.6 (99.3) |
| Redundancy | 11.0 (5.3) | 6.5 (5.2) |
| Refinement | | |
| Resolution (Å) | 35.4-1.6 (1.62-1.60) | 42.2-3.6 (3.88-3.60) |
| No. reflections | 63,360 (2,241) | 13,877 (2,742) |
| Rwork/Rfree (%) | 24.1/25.5 | 21.3/26.7 |
| No. atoms | | |
| Protein | 3,305 | 6,778 |
| Ligand/ion | 0 | 0 |
| Water | 270 | 0 |
| B-factors | | |
| Protein | 53.0 | 128.1 |
| Ligand/ion | — | — |
| Water | 44.1 | — |
| R.m.s. deviations | | |
| Bond lengths (Å) | 0.007 | 0.003 |
| Bond angles (°) | 1.20 | 0.91 |
| Ramachandran | | |
| Favored (%) | 96.5 | 92.0 |
| Allowed (%) | 3.0 | 7.3 |
| Outliers (%) | 0.5 | 0.7 |

Figure 14:
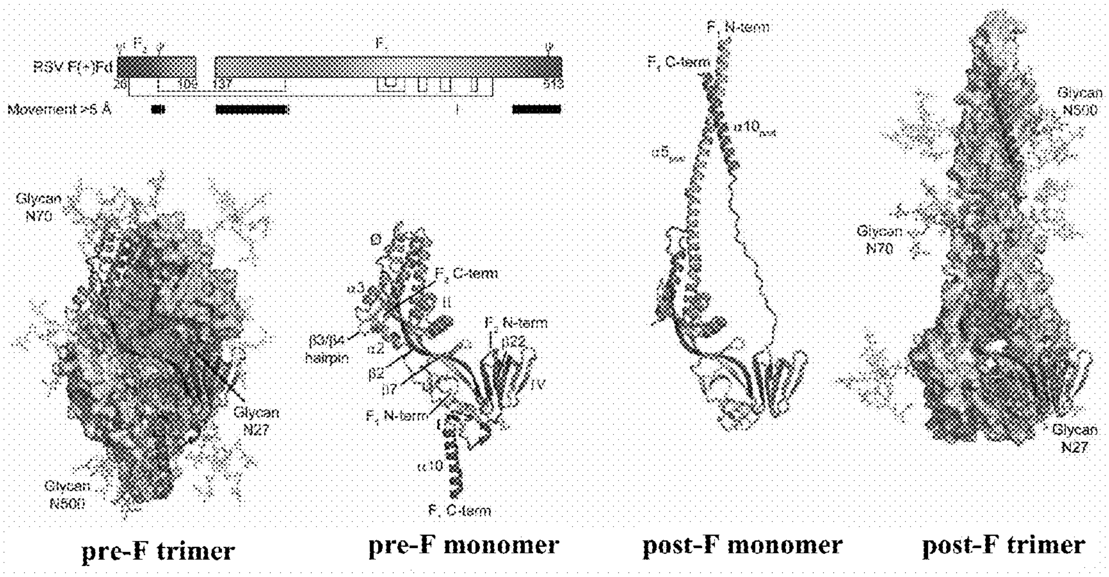
FIG. 14 shows the crystal structures of the monomer and trimer of pre-F protein as well as of the monomer and trimer of post-F protein. The results show that pre-F protein and post-F protein are significantly different from each other in terms of spatial structure (conformation).

In addition, the same method was used to analyze the crystal structures of the monomer and trimer of pre-F protein as well as of the monomer and trimer of post-F protein. The results in FIG. 14 showed that pre-F protein and post-F protein were significantly different from each other in terms of spatial structure (conformation).

Figure 11:
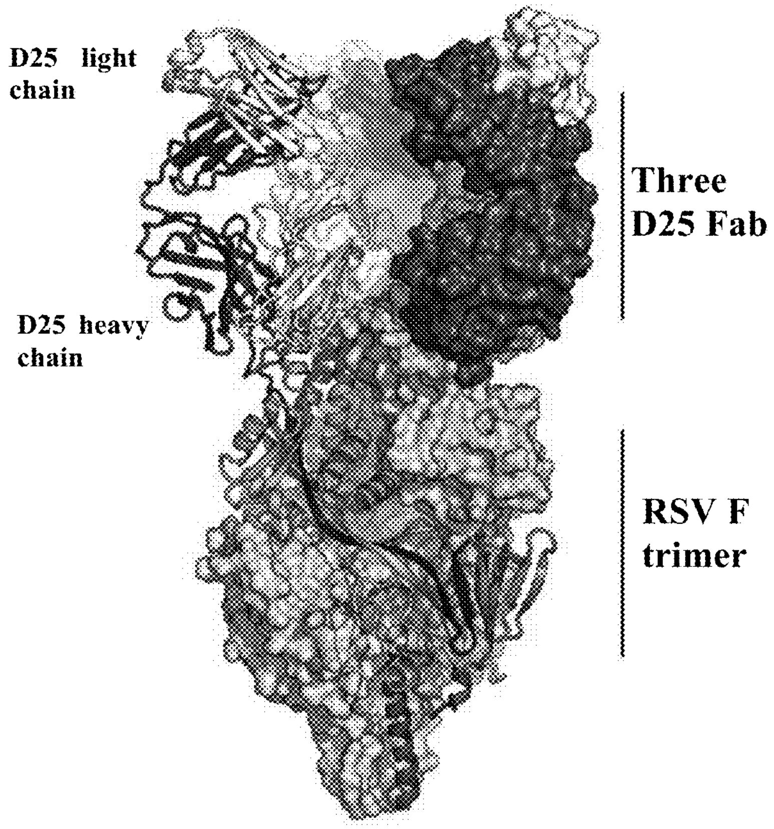
FIG. 11 shows the crystal structure of D25/F protein complex.
Figure 12:
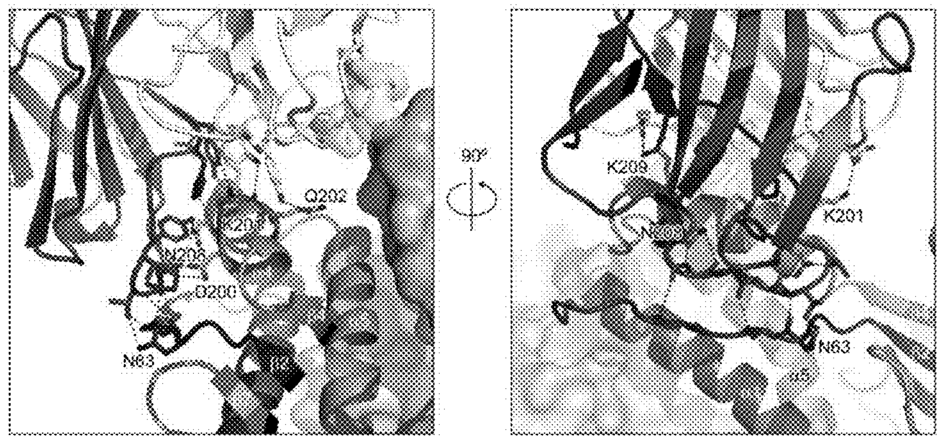
FIG. 12 shows the spatial structure of the binding interface between D25 monoclonal antibody and the epitope of F protein.
Figure 13:
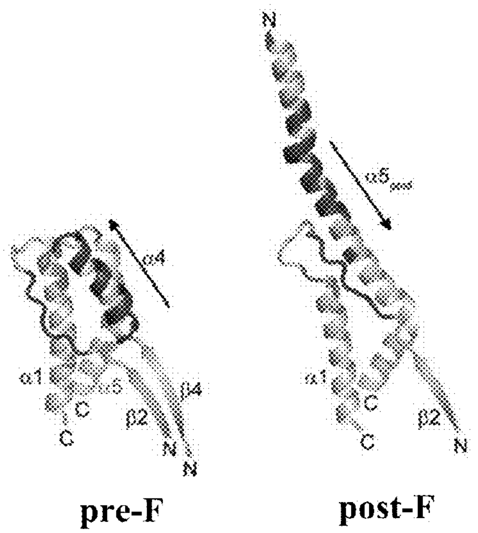
FIG. 13 shows change of the tertiary structure of D25-binding epitope on pre-F protein and post-F protein molecules.

The results of X-ray diffraction and structure determination of the complex crystals show that D25 monoclonal antibody binds an epitope spanning two protomers at the apex of the pre-F trimer, wherein the heavy chain of D25 binds to a monomer, and the light chain binds to another monomer close to the monomer (as shown in FIG. 11-12). 5 of 6 CDRs of D25 antibody bind to RSV F protein, wherein the heavy chain CDR3 binds to α4 helix of F protein (consisting of the amino acid residues from positions 196 to 209 of F protein) and binds to the loop structure (consisting of the amino acid residues from positions 62 to 72 of F protein) between β2 sheet (consisting of the amino acid residues from positions 38 to 60 of F protein) and α1 helix (consisting of the amino acid residues from positions 74 to 96 of F protein). The epitope recognized by D25 is not greatly changed between the secondary structures of pre-F protein and post-F protein, but is significantly changed between the tertiary structures of pre-F protein and post-F protein, i.e. α4 helix turns 180° and is far from β2 sheet (as shown in FIG. 13). The change in the tertiary structure of the epitope bound by D25 shows why D25 antibody binds to pre-F protein but not to post-F protein, and explains why D25 antibody can stabilize the structure of pre-F protein and thus neutralize RSV.

As the results in FIGS. 11-13 and Table 2, it was determined that the epitope of F protein, recognized by D25 monoclonal antibody, consists of the amino acid residues a.a. 148 to 216 of RSV fusion protein or a fragment thereof, and at least comprises the amino acid residues a.a. 196 to 209 of RSV fusion protein. In addition, it is found that the amino acid residues from a.a. 62 to 69 or a.a. 62 to 76 of RSV fusion protein can promote the specific binding of D25 monoclonal antibody/F protein. It could be determined by a similar method that AM22 monoclonal antibody and 5C4 monoclonal antibody also recognize said epitope of F protein.

The results are also shown in FIG. 15. FIG. 15 shows the structures of pre-F protein and post-F protein, the corresponding amino acid sequences that constitutes the spatial structures, and the sequence of the epitope recognized by D25. The results in FIG. 15 show that there is a significant difference between the tertiary structures of pre-F protein and post-F protein. Particularly, the spatialstructure of pre-F protein includes α1-α10 helixes and β1-β23 sheets; while the spatialstructure of post-F protein includes al helix, α5-α8 helixes, α10 helix, β1-β2 sheets and β5-β21 sheets.

In addition, the results in FIG. 15 also show that the core epitope of pre-F protein, recognized by D25 monoclonal antibody, is the two peptide segments that are sterically close to each other, i.e. a.a. 62-69 and a.a. 196-209. The interacting interface of the two peptide segments shows that two segments of F protein (a.a.62-76 and a.a.137-216 (or more particularly, a.a.148-216)) or fragments thereof have an important effect on the recognition and stabilization of pre-F protein by such antibodies (such as, the antibodies of the invention (e.g. 5C4), D25 and AM22), wherein the two regions a.a.176-181 and a.a.185-194 have a significant change between pre-F conformation and post-F conformation of F protein, i.e. they are in a conformation of β sheet (β3-β4 sheet) in pre-F protein, but are in a conformation of a helix (comprised in α5 helix) in post-F protein.

These results show that D25 monoclonal antibody, AM22 monoclonal antibody and 5C4 monoclonal antibody recognize the same epitope on F protein, and stabilized and maintain the pre-F conformation of F protein by interacting with the epitope. The new epitope and the antibodies recognizing the epitope as discovered in the invention can stabilize the pre-F conformation of F protein.

In addition, the above results show that the antibodies recognizing the epitope have a higher neutralizing activity. This indicates that pre-F conformation of the F protein and the new epitope play an important role in inducing a strong immune response in organisms, and the antibodies recognizing the epitope can effectively prevent and treat RSV infection and diseases associated with RSV infection.

Although the specific embodiments of the invention have been described in detail, those skilled in the art would understand that, according to all the disclosed teachings, various modifications and changes can be made, and that such modifications and changes are within the scope of the present invention. The scope of the present invention is given by the appended claims and any equivalents thereof.

The invention claimed is:

1. A monoclonal antibody and an antigen binding fragment thereof, wherein the monoclonal antibody can specifically bind to amino acid residues from positions 148 to 216 of respiratory syncytial virus (RSV) fusion protein (F protein) or a fragment thereof, and/or amino acid residues from positions 62 to 69 or positions 62 to 76 of RSV F protein, wherein the monoclonal antibody comprises the following CDRs: 1) a heavy chain CDR1 set forth in SEQ ID NO:20; 2) a heavy chain CDR2 set forth in SEQ ID NO:21; 3) a heavy chain CDR3 set forth in SEQ ID NO:22; 4) a light chain CDR1 set forth in SEQ ID NO:23; 5) a light chain CDR2 set forth in SEQ ID NO:24; and, 6) a light chain CDR3 set forth in SEQ ID NO:25, and the F protein has an amino acid sequence as set forth in SEQ ID NO. 15.

2. An isolated nucleic acid molecule, encoding the monoclonal antibody or antigen binding fragment thereof according to claim 1.

3. A vector, comprising the isolated nucleic acid molecule according to claim 2.

4. A host cell, comprising the isolated nucleic acid molecule according to claim 2 or a vector comprising the isolated nucleic acid molecule.

5. A hybridoma cell line RSV-Y-5C4-2, which is deposited in China Center for Type Culture Collection (CCTCC), and has a deposit number of CCTCC NO: C2012147.

6. A method for stabilizing pre-F protein, comprising contacting the monoclonal antibody or antigen binding fragment thereof according to claim 1 with a sample comprising pre-F protein.

7. A kit comprising the monoclonal antibody or antigen binding fragment thereof according to claim 1.

8. A pharmaceutical composition comprising the monoclonal antibody or antigen binding fragment thereof according to claim 1, and a pharmaceutically acceptable carrier and/or excipient.

9. A method for preventing or treating RSV infection, comprising administering a prophylactically or therapeutically effective amount of the monoclonal antibody or antigen binding fragment thereof according to claim 1 to a subject in need thereof.

10. A method for expressing pre-F protein or an antigen-antibody complex, comprising co-expressing a nucleic acid encoding the monoclonal antibody or antigen binding fragment thereof according to claim 1, and a nucleic acid encoding F protein in a cell.

11. A kit comprising a nucleic acid encoding the monoclonal antibody or antigen binding fragment thereof according to claim 1, and a nucleic acid encoding F protein.

12. The monoclonal antibody or antigen binding fragment thereof according to claim 1, wherein the monoclonal antibody has one or more of the following features:

(1) the monoclonal antibody comprises a) a heavy chain variable region set forth in SEQ ID NO:17; and b) a light chain variable region set forth in SEQ ID NO:19;

(2) the monoclonal antibody or antigen binding fragment thereof is selected from Fab, Fab', F(ab')2, Fd, Fv, dAb, complementary determining region fragment, single chain antibody, mouse antibody, humanized antibody, chimeric antibody, or bispecific or poly-specific antibody, (3) the monoclonal antibody comprises non-CDR region, and the non-CDR region is from species other than murine species;

(4) the monoclonal antibody specifically binds to RSV, and has a neutralizing activity for the virus;

(5) the monoclonal antibody does not bind to post-F protein, but binds and stabilizes pre-F protein; and (6) the monoclonal antibody is derived from or is the following monoclonal antibody: monoclonal antibody produced by hybridoma cell line RSV-Y-5C4-2, wherein hybridoma cell line RSV-Y-5C4-2 is deposited in China Center for Type Culture Collection (CCTCC), and has a deposit number of CCTCC NO: C2012147.

13. The monoclonal antibody or antigen binding fragment thereof according to claim 12, wherein the single chain antibody is scFv.

14. The monoclonal antibody or antigen binding fragment thereof according to claim 12, wherein the chimeric antibody is human mouse chimeric antibody.

15. The monoclonal antibody or antigen binding fragment thereof according to claim 12, wherein the non-CDR region is from human antibody.

16. A method for detecting the presence or level of pre-F protein in a sample, comprising the steps of contacting the monoclonal antibody or antigen binding fragment thereof according to claim 1 with a sample having or suspected to have pre-F protein, and detecting any binding between the monoclonal antibody or antigen binding fragment thereof and pre-F protein.

17. A method for diagnosing whether a subject is infected by RSV, comprising the steps of contacting the monoclonal antibody or antigen binding fragment thereof according to claim 1 with a sample from a subject that is suspected to be infected by RSV, and detecting the presence of RSV in the sample by detecting any binding between the monoclonal antibody or antigen binding fragment thereof and pre-F protein of RSV.

* * * * *

SEQUENCE LISTING

```
<160> NUMBER OF SEQ ID NOS: 57

<210> SEQ ID NO 1
<211> LENGTH: 14
<212> TYPE: PRT
<213> ORGANISM: Artificial sequence
<220> FEATURE:
<223> OTHER INFORMATION: amino acid sequence from positions 196 to 209
      of F protein

<400> SEQUENCE: 1

Lys Asn Tyr Ile Asp Lys Gln Leu Leu Pro Ile Val Asn Lys
1               5                   10


<210> SEQ ID NO 2
<211> LENGTH: 14
<212> TYPE: PRT
<213> ORGANISM: Artificial sequence
<220> FEATURE:
<223> OTHER INFORMATION: variant of the amino acid sequence from
      positions 196 to 209 of F protein

<400> SEQUENCE: 2

Lys Asn Tyr Ile Asn Asn Gln Leu Leu Pro Ile Val Asn Gln
1               5                   10


<210> SEQ ID NO 3
<211> LENGTH: 21
<212> TYPE: PRT
<213> ORGANISM: Artificial sequence
<220> FEATURE:
<223> OTHER INFORMATION: amino acid sequence from positions 196 to 216
      of F protein

<400> SEQUENCE: 3

Lys Asn Tyr Ile Asp Lys Gln Leu Leu Pro Ile Val Asn Lys Gln Ser
1               5                   10                  15

Cys Ser Ile Ser Asn
            20


<210> SEQ ID NO 4
<211> LENGTH: 21
<212> TYPE: PRT
<213> ORGANISM: Artificial sequence
<220> FEATURE:
<223> OTHER INFORMATION: variant of the amino acid sequence from
      positions 196 to 216 of F protein

<400> SEQUENCE: 4

Lys Asn Tyr Ile Asn Asn Gln Leu Leu Pro Ile Val Asn Gln Gln Ser
1               5                   10                  15

Cys Arg Ile Ser Asn
            20


<210> SEQ ID NO 5
<211> LENGTH: 32
<212> TYPE: PRT
<213> ORGANISM: Artificial sequence
<220> FEATURE:
<223> OTHER INFORMATION: amino acid sequence from positions 185 to 216
      of F protein

<400> SEQUENCE: 5

Val Ser Val Leu Thr Ser Lys Val Leu Asp Leu Lys Asn Tyr Ile Asp
1               5                   10                  15

Lys Gln Leu Leu Pro Ile Val Asn Lys Gln Ser Cys Ser Ile Ser Asn
```

20 25 30

<210> SEQ ID NO 6
<211> LENGTH: 32
<212> TYPE: PRT
<213> ORGANISM: Artificial sequence
<220> FEATURE:
<223> OTHER INFORMATION: variant of the amino acid sequence from positions 185 to 216 of F protein

<400> SEQUENCE: 6

Val Ser Val Leu Thr Ser Lys Val Leu Asp Leu Lys Asn Tyr Ile Asn
1 5 10 15

Asn Gln Leu Leu Pro Ile Val Asn Gln Gln Ser Cys Arg Ile Ser Asn
20 25 30

<210> SEQ ID NO 7
<211> LENGTH: 41
<212> TYPE: PRT
<213> ORGANISM: Artificial sequence
<220> FEATURE:
<223> OTHER INFORMATION: amino acid sequence from positions 176 to 216 of F protein

<400> SEQUENCE: 7

Lys Ala Val Val Ser Leu Ser Asn Gly Val Ser Val Leu Thr Ser Lys
1 5 10 15

Val Leu Asp Leu Lys Asn Tyr Ile Asp Lys Gln Leu Leu Pro Ile Val
20 25 30

Asn Lys Gln Ser Cys Ser Ile Ser Asn
35 40

<210> SEQ ID NO 8
<211> LENGTH: 41
<212> TYPE: PRT
<213> ORGANISM: Artificial sequence
<220> FEATURE:
<223> OTHER INFORMATION: variant of the amino acid sequence from positions 176 to 216 of F protein

<400> SEQUENCE: 8

Lys Ala Val Val Ser Leu Ser Asn Gly Val Ser Val Leu Thr Ser Lys
1 5 10 15

Val Leu Asp Leu Lys Asn Tyr Ile Asn Asn Gln Leu Leu Pro Ile Val
20 25 30

Asn Gln Gln Ser Cys Arg Ile Ser Asn
35 40

<210> SEQ ID NO 9
<211> LENGTH: 69
<212> TYPE: PRT
<213> ORGANISM: Artificial sequence
<220> FEATURE:
<223> OTHER INFORMATION: amino acid sequence from positions 148 to 216 of F protein

<400> SEQUENCE: 9

Ile Ala Ser Gly Ile Ala Val Ser Lys Val Leu His Leu Glu Gly Glu
1 5 10 15

Val Asn Lys Ile Lys Ser Ala Leu Leu Ser Thr Asn Lys Ala Val Val
20 25 30

Ser Leu Ser Asn Gly Val Ser Val Leu Thr Ser Lys Val Leu Asp Leu
35 40 45

```
Lys Asn Tyr Ile Asp Lys Gln Leu Leu Pro Ile Val Asn Lys Gln Ser
    50                  55                  60

Cys Ser Ile Ser Asn
65


<210> SEQ ID NO 10
<211> LENGTH: 69
<212> TYPE: PRT
<213> ORGANISM: Artificial sequence
<220> FEATURE:
<223> OTHER INFORMATION: variant of the amino acid sequence from
      positions 148 to 216 of F protein

<400> SEQUENCE: 10

Ile Ala Ser Gly Ile Ala Val Ser Lys Val Leu His Leu Glu Gly Glu
1               5                   10                  15

Val Asn Lys Ile Lys Asn Ala Leu Leu Ser Thr Asn Lys Ala Val Val
            20                  25                  30

Ser Leu Ser Asn Gly Val Ser Val Leu Thr Ser Lys Val Leu Asp Leu
        35                  40                  45

Lys Asn Tyr Ile Asn Asn Gln Leu Leu Pro Ile Val Asn Gln Gln Ser
    50                  55                  60

Cys Arg Ile Ser Asn
65


<210> SEQ ID NO 11
<211> LENGTH: 8
<212> TYPE: PRT
<213> ORGANISM: Artificial sequence
<220> FEATURE:
<223> OTHER INFORMATION: amino acid sequence from positions 62 to 69 of
      F protein

<400> SEQUENCE: 11

Ser Asn Ile Lys Glu Asn Lys Cys
1               5


<210> SEQ ID NO 12
<211> LENGTH: 8
<212> TYPE: PRT
<213> ORGANISM: Artificial sequence
<220> FEATURE:
<223> OTHER INFORMATION: variant of the amino acid sequence from
      positions 62 to 69 of F protein

<400> SEQUENCE: 12

Ser Asn Ile Lys Glu Thr Lys Cys
1               5


<210> SEQ ID NO 13
<211> LENGTH: 15
<212> TYPE: PRT
<213> ORGANISM: Artificial sequence
<220> FEATURE:
<223> OTHER INFORMATION: amino acid sequence from positions 62 to 76 of
      F protein

<400> SEQUENCE: 13

Ser Asn Ile Lys Glu Asn Lys Cys Asn Gly Thr Asp Ala Lys Val
1               5                   10                  15


<210> SEQ ID NO 14
<211> LENGTH: 15
<212> TYPE: PRT
<213> ORGANISM: Artificial sequence
```

```
<220> FEATURE:
<223> OTHER INFORMATION: variant of the amino acid sequence from
      positions 62 to 76 of F protein

<400> SEQUENCE: 14

Ser Asn Ile Lys Glu Thr Lys Cys Asn Gly Thr Asp Thr Lys Val
1               5                   10                  15


<210> SEQ ID NO 15
<211> LENGTH: 574
<212> TYPE: PRT
<213> ORGANISM: Artificial sequence
<220> FEATURE:
<223> OTHER INFORMATION: amino acid sequence of F protein

<400> SEQUENCE: 15

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Pro Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320
```

```
Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 16
<211> LENGTH: 413
<212> TYPE: DNA
<213> ORGANISM: Artificial sequence
<220> FEATURE:
<223> OTHER INFORMATION: nucleotide sequence of 5C4 heavy chain variable region

<400> SEQUENCE: 16

```
gaggttcagc tgcagcagtc tggggcagag cttgtgaagc caggggcctc agtcaagttg     60

tcctgcacag cttctggctt caacattaaa gacacctttt ttcactgggt gaagcagagg    120

cctgaacagg gcctggagtg gattggaagg attgatcctg cggatggtca tactaaatat    180

gacccgaagt tccagggcaa ggccactata acagcagaca catcctccaa cacagccttc    240

ctgcagctca gcagcctgac atctgaggac actgccgtct attactgtgc tactactatt    300

actgcggttg tacctacccc ttacaatgct atggactatt ggggtcaagg aacctcagtc    360

accgtctcct cagccaaaac aacagcccca cctgtttatc cattggcccc tgg           413
```

<210> SEQ ID NO 17
<211> LENGTH: 137
<212> TYPE: PRT
<213> ORGANISM: Artificial sequence
<220> FEATURE:

<223> OTHER INFORMATION: amino acid sequence of 5C4 heavy chain variable region

<400> SEQUENCE: 17

```
Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Phe Phe His Trp Val Lys Gln Arg Pro Glu Gln Gly Leu Glu Trp Ile
        35                  40                  45

Gly Arg Ile Asp Pro Ala Asp Gly His Thr Lys Tyr Asp Pro Lys Phe
    50                  55                  60

Gln Gly Lys Ala Thr Ile Thr Ala Asp Thr Ser Ser Asn Thr Ala Phe
65                  70                  75                  80

Leu Gln Leu Ser Ser Leu Thr Ser Glu Asp Thr Ala Val Tyr Tyr Cys
                85                  90                  95

Ala Thr Thr Ile Thr Ala Val Val Pro Thr Pro Tyr Asn Ala Met Asp
            100                 105                 110

Tyr Trp Gly Gln Gly Thr Ser Val Thr Val Ser Ser Ala Lys Thr Thr
        115                 120                 125

Ala Pro Pro Val Tyr Pro Leu Ala Pro
    130                 135
```

<210> SEQ ID NO 18
<211> LENGTH: 378
<212> TYPE: DNA
<213> ORGANISM: Artificial sequence
<220> FEATURE:
<223> OTHER INFORMATION: nucleotide sequence of 5C4 light chain variable region

<400> SEQUENCE: 18

```
gacattgtgc tgacccaatc tccagcttct ttggctgtgt ctctagggca gaggaccacc      60

atatcctgca gagccagtga aagtgttgat agttttgaca atagttttat acactggtac     120

cagcagaaac caggacagcc acccaaactc ctcatctttc ttgcatccag cctagaatct     180

ggggtccctg ccaggttcag tggcagtggg tctaggactg acttcaccct caccattgat     240

cctgtggagg ctgatgatgc tgcaacctat tactgtcagc aaagtaatga ggatccattc     300

acgttcggct cggggacaaa gttggaaata aaacgggctg atgctgcacc aactgtatcc     360

atcttcccac catccagt                                                   378
```

<210> SEQ ID NO 19
<211> LENGTH: 126
<212> TYPE: PRT
<213> ORGANISM: Artificial sequence
<220> FEATURE:
<223> OTHER INFORMATION: amino acid sequence of 5C4 light chain variable region

<400> SEQUENCE: 19

```
Asp Ile Val Leu Thr Gln Ser Pro Ala Ser Leu Ala Val Ser Leu Gly
1               5                   10                  15

Gln Arg Thr Thr Ile Ser Cys Arg Ala Ser Glu Ser Val Asp Ser Phe
            20                  25                  30

Asp Asn Ser Phe Ile His Trp Tyr Gln Gln Lys Pro Gly Gln Pro Pro
        35                  40                  45

Lys Leu Leu Ile Phe Leu Ala Ser Ser Leu Glu Ser Gly Val Pro Ala
    50                  55                  60
```

Arg Phe Ser Gly Ser Gly Ser Arg Thr Asp Phe Thr Leu Thr Ile Asp
65 70 75 80

Pro Val Glu Ala Asp Asp Ala Ala Thr Tyr Tyr Cys Gln Gln Ser Asn
85 90 95

Glu Asp Pro Phe Thr Phe Gly Ser Gly Thr Lys Leu Glu Ile Lys Arg
100 105 110

Ala Asp Ala Ala Pro Thr Val Ser Ile Phe Pro Pro Ser Ser
115 120 125

<210> SEQ ID NO 20
<211> LENGTH: 8
<212> TYPE: PRT
<213> ORGANISM: Artificial sequence
<220> FEATURE:
<223> OTHER INFORMATION: 5C4 heavy chain CDR1

<400> SEQUENCE: 20

Gly Phe Asn Ile Lys Asp Thr Phe
1 5

<210> SEQ ID NO 21
<211> LENGTH: 8
<212> TYPE: PRT
<213> ORGANISM: Artificial sequence
<220> FEATURE:
<223> OTHER INFORMATION: 5C4 heavy chain CDR2

<400> SEQUENCE: 21

Ile Asp Pro Ala Asp Gly His Thr
1 5

<210> SEQ ID NO 22
<211> LENGTH: 17
<212> TYPE: PRT
<213> ORGANISM: Artificial sequence
<220> FEATURE:
<223> OTHER INFORMATION: 5C4 heavy chain CDR3

<400> SEQUENCE: 22

Ala Thr Thr Ile Thr Ala Val Val Pro Thr Pro Tyr Asn Ala Met Asp
1 5 10 15

Tyr

<210> SEQ ID NO 23
<211> LENGTH: 10
<212> TYPE: PRT
<213> ORGANISM: Artificial sequence
<220> FEATURE:
<223> OTHER INFORMATION: 5C4 light chain CDR1

<400> SEQUENCE: 23

Glu Ser Val Asp Ser Phe Asp Asn Ser Phe
1 5 10

<210> SEQ ID NO 24
<211> LENGTH: 3
<212> TYPE: PRT
<213> ORGANISM: Artificial sequence
<220> FEATURE:
<223> OTHER INFORMATION: 5C4 light chain CDR2

<400> SEQUENCE: 24

Leu Ala Ser
1

<210> SEQ ID NO 25
<211> LENGTH: 9
<212> TYPE: PRT
<213> ORGANISM: Artificial sequence
<220> FEATURE:
<223> OTHER INFORMATION: 5C4 light chain CDR3

<400> SEQUENCE: 25

Gln Gln Ser Asn Glu Asp Pro Phe Thr
1 5

<210> SEQ ID NO 26
<211> LENGTH: 26
<212> TYPE: DNA
<213> ORGANISM: Artificial sequence
<220> FEATURE:
<223> OTHER INFORMATION: primer

<400> SEQUENCE: 26
atgraatgsa sctgggtywt yctctt 26

<210> SEQ ID NO 27
<211> LENGTH: 29
<212> TYPE: DNA
<213> ORGANISM: Artificial sequence
<220> FEATURE:
<223> OTHER INFORMATION: primer

<400> SEQUENCE: 27
atggactcca ggctcaattt agttttcct 29

<210> SEQ ID NO 28
<211> LENGTH: 26
<212> TYPE: DNA
<213> ORGANISM: Artificial sequence
<220> FEATURE:
<223> OTHER INFORMATION: primer

<400> SEQUENCE: 28
atggctgtcy trgbgctgyt cytctg 26

<210> SEQ ID NO 29
<211> LENGTH: 29
<212> TYPE: DNA
<213> ORGANISM: Artificial sequence
<220> FEATURE:
<223> OTHER INFORMATION: primer

<400> SEQUENCE: 29
atggvttggs tgtggamctt gcyattcct 29

<210> SEQ ID NO 30
<211> LENGTH: 26
<212> TYPE: DNA
<213> ORGANISM: Artificial sequence
<220> FEATURE:
<223> OTHER INFORMATION: primer

<400> SEQUENCE: 30
atgaaatgca gctggrtyat sttctt 26

<210> SEQ ID NO 31
<211> LENGTH: 26
<212> TYPE: DNA
<213> ORGANISM: Artificial sequence
<220> FEATURE:
<223> OTHER INFORMATION: primer

<400> SEQUENCE: 31
atggrcagrc ttacwtyytc attcct 26

<210> SEQ ID NO 32
<211> LENGTH: 26
<212> TYPE: DNA
<213> ORGANISM: Artificial sequence
<220> FEATURE:
<223> OTHER INFORMATION: primer

<400> SEQUENCE: 32
atgatggtgt taagtcttct gtacct 26

<210> SEQ ID NO 33
<211> LENGTH: 26
<212> TYPE: DNA
<213> ORGANISM: Artificial sequence
<220> FEATURE:
<223> OTHER INFORMATION: primer

<400> SEQUENCE: 33
atgggatgga gctrtatcat sytctt 26

<210> SEQ ID NO 34
<211> LENGTH: 23
<212> TYPE: DNA
<213> ORGANISM: Artificial sequence
<220> FEATURE:
<223> OTHER INFORMATION: primer

<400> SEQUENCE: 34
atgaagwtgt ggbtraactg grt 23

<210> SEQ ID NO 35
<211> LENGTH: 24
<212> TYPE: DNA
<213> ORGANISM: Artificial sequence
<220> FEATURE:
<223> OTHER INFORMATION: primer

<400> SEQUENCE: 35
atggratgga sckkrtcttt mtct 24

<210> SEQ ID NO 36
<211> LENGTH: 25
<212> TYPE: DNA
<213> ORGANISM: Artificial sequence
<220> FEATURE:
<223> OTHER INFORMATION: primer

<400> SEQUENCE: 36
atgaacttyg ggytsagmtt grttt 25

<210> SEQ ID NO 37
<211> LENGTH: 25
<212> TYPE: DNA
<213> ORGANISM: Artificial sequence
<220> FEATURE:
<223> OTHER INFORMATION: primer

<400> SEQUENCE: 37
atgtacttgg gactgagctg tgtat 25

-continued

<210> SEQ ID NO 38
<211> LENGTH: 23
<212> TYPE: DNA
<213> ORGANISM: Artificial sequence
<220> FEATURE:
<223> OTHER INFORMATION: primer

<400> SEQUENCE: 38
atgagagtgc tgattctttt gtg 23

<210> SEQ ID NO 39
<211> LENGTH: 28
<212> TYPE: DNA
<213> ORGANISM: Artificial sequence
<220> FEATURE:
<223> OTHER INFORMATION: primer

<400> SEQUENCE: 39
atggattttg ggctgatttt ttttattg 28

<210> SEQ ID NO 40
<211> LENGTH: 26
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (21)..(21)
<223> OTHER INFORMATION: n is a, c, g, or t

<400> SEQUENCE: 40
ccagggrcca rkggatarca ngrtgg 26

<210> SEQ ID NO 41
<211> LENGTH: 24
<212> TYPE: DNA
<213> ORGANISM: Artificial sequence
<220> FEATURE:
<223> OTHER INFORMATION: primer

<400> SEQUENCE: 41
atgragwcac akwcycaggt cttt 24

<210> SEQ ID NO 42
<211> LENGTH: 25
<212> TYPE: DNA
<213> ORGANISM: Artificial sequence
<220> FEATURE:
<223> OTHER INFORMATION: primer

<400> SEQUENCE: 42
atggagacag acacactcct gctat 25

<210> SEQ ID NO 43
<211> LENGTH: 29
<212> TYPE: DNA
<213> ORGANISM: Artificial sequence
<220> FEATURE:
<223> OTHER INFORMATION: primer

<400> SEQUENCE: 43
atggagwcag acacactsct gytatgggt 29

<210> SEQ ID NO 44
<211> LENGTH: 31

```
<212> TYPE: DNA
<213> ORGANISM: Artificial sequence
<220> FEATURE:
<223> OTHER INFORMATION: primer

<400> SEQUENCE: 44

atgaggrccc ctgctcagwt tyttggwtct t                                    31


<210> SEQ ID NO 45
<211> LENGTH: 31
<212> TYPE: DNA
<213> ORGANISM: Artificial sequence
<220> FEATURE:
<223> OTHER INFORMATION: primer

<400> SEQUENCE: 45

atgggcwtca agatgragtc acakwyycwg g                                    31


<210> SEQ ID NO 46
<211> LENGTH: 29
<212> TYPE: DNA
<213> ORGANISM: Artificial sequence
<220> FEATURE:
<223> OTHER INFORMATION: primer

<400> SEQUENCE: 46

atgagtgtgc ycactcaggt cctggsgtt                                       29


<210> SEQ ID NO 47
<211> LENGTH: 31
<212> TYPE: DNA
<213> ORGANISM: Artificial sequence
<220> FEATURE:
<223> OTHER INFORMATION: primer

<400> SEQUENCE: 47

atgtggggay cgktttyamm cttttcaatt g                                    31


<210> SEQ ID NO 48
<211> LENGTH: 28
<212> TYPE: DNA
<213> ORGANISM: Artificial sequence
<220> FEATURE:
<223> OTHER INFORMATION: primer

<400> SEQUENCE: 48

atggaagccc cagctcagct tctcttcc                                        28


<210> SEQ ID NO 49
<211> LENGTH: 23
<212> TYPE: DNA
<213> ORGANISM: Artificial sequence
<220> FEATURE:
<223> OTHER INFORMATION: primer

<400> SEQUENCE: 49

atgagmmktc mttcattcyt ggg                                             23


<210> SEQ ID NO 50
<211> LENGTH: 24
<212> TYPE: DNA
<213> ORGANISM: Artificial sequence
<220> FEATURE:
<223> OTHER INFORMATION: primer

<400> SEQUENCE: 50
```

-continued atgakgthcy cgctcagyty ctrg 24

<210> SEQ ID NO 51
<211> LENGTH: 25
<212> TYPE: DNA
<213> ORGANISM: Artificial sequence
<220> FEATURE:
<223> OTHER INFORMATION: primer

<400> SEQUENCE: 51
atggtrtccw casctcagtt ccttg 25

<210> SEQ ID NO 52
<211> LENGTH: 27
<212> TYPE: DNA
<213> ORGANISM: Artificial sequence
<220> FEATURE:
<223> OTHER INFORMATION: primer

<400> SEQUENCE: 52
atgtatatat gtttgttgtc tatttct 27

<210> SEQ ID NO 53
<211> LENGTH: 29
<212> TYPE: DNA
<213> ORGANISM: Artificial sequence
<220> FEATURE:
<223> OTHER INFORMATION: primer

<400> SEQUENCE: 53
atgaagttgc ctgttaggct gttggtgct 29

<210> SEQ ID NO 54
<211> LENGTH: 29
<212> TYPE: DNA
<213> ORGANISM: Artificial sequence
<220> FEATURE:
<223> OTHER INFORMATION: primer

<400> SEQUENCE: 54
atggatttwc argtgcagat twtcagctt 29

<210> SEQ ID NO 55
<211> LENGTH: 27
<212> TYPE: DNA
<213> ORGANISM: Artificial sequence
<220> FEATURE:
<223> OTHER INFORMATION: primer

<400> SEQUENCE: 55
atggtyctya tvtccttgct gttctgg 27

<210> SEQ ID NO 56
<211> LENGTH: 27
<212> TYPE: DNA
<213> ORGANISM: Artificial sequence
<220> FEATURE:
<223> OTHER INFORMATION: primer

<400> SEQUENCE: 56
atggtyctya tvttrctgct gctatgg 27

<210> SEQ ID NO 57
<211> LENGTH: 21
<212> TYPE: DNA
<213> ORGANISM: Artificial sequence -continued

```
<220> FEATURE:
<223> OTHER INFORMATION: primer

<400> SEQUENCE: 57

actggatggt gggaagatgg a                                              21
```